(12) United States Patent
Burkly et al.

(10) Patent No.: US 8,728,475 B2
(45) Date of Patent: May 20, 2014

(54) METHODS FOR TREATING INFLAMMATORY BOWEL DISEASE

(75) Inventors: Linda C. Burkly, West Newton, MA (US); Timothy Zheng, Boston, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 13/246,197

(22) Filed: Sep. 27, 2011

(65) Prior Publication Data

US 2012/0014953 A1    Jan. 19, 2012

Related U.S. Application Data

(63) Continuation of application No. 11/937,687, filed on Nov. 9, 2007, now abandoned, which is a continuation of application No. PCT/US2006/018077, filed on May 10, 2006.

(60) Provisional application No. 60/679,518, filed on May 10, 2005.

(51) Int. Cl.
*A61K 39/395* (2006.01)
*A61K 38/16* (2006.01)
*A61K 38/17* (2006.01)

(52) U.S. Cl.
USPC ............. 424/145.1; 424/133.1; 424/141.1; 424/142.1; 514/13.2; 514/21.2

(58) Field of Classification Search
None
See application file for complete search history.

(56) References Cited

U.S. PATENT DOCUMENTS

| | | | |
|---|---|---|---|
| 4,777,245 A | 10/1988 | Foung et al. |
| 4,921,698 A | 5/1990 | Shirai et al. |
| 5,073,492 A | 12/1991 | Chen et al. |
| 5,200,313 A | 4/1993 | Carrico |
| 5,223,409 A | 6/1993 | Ladner et al. |
| 5,225,539 A | 7/1993 | Winter |
| 5,624,821 A | 4/1997 | Winter et al. |
| 5,648,260 A | 7/1997 | Winter et al. |
| 5,693,762 A | 12/1997 | Queen et al. |
| 5,858,991 A | 1/1999 | Hellerqvist et al. |
| 5,859,205 A | 1/1999 | Adair et al. |
| 5,877,015 A | 3/1999 | Hardy et al. |
| 5,885,793 A | 3/1999 | Griffiths et al. |
| 6,037,521 A | 3/2000 | Sato et al. |
| 6,046,381 A | 4/2000 | Mucke et al. |
| 6,207,642 B1 | 3/2001 | Wiley |
| 6,258,562 B1 | 7/2001 | Salfeld et al. |
| 6,300,064 B1 | 10/2001 | Knappik et al. |
| 6,407,213 B1 | 6/2002 | Carter et al. |
| 6,448,042 B1 | 9/2002 | Greene et al. |
| 6,492,123 B1 | 12/2002 | Holliger et al. |
| 6,531,447 B1 | 3/2003 | Ruben et al. |
| 6,544,761 B2 | 4/2003 | Greene et al. |
| 6,572,852 B2 | 6/2003 | Smith et al. |
| 6,608,048 B2 | 8/2003 | Tsou et al. |
| 6,630,514 B2 | 10/2003 | Youdim et al. |
| 6,727,225 B2 | 4/2004 | Wiley |
| 6,824,773 B2 | 11/2004 | Wiley |
| 6,943,146 B2 | 9/2005 | Jakubowski et al. |
| 7,001,992 B2 | 2/2006 | Ruben et al. |
| 7,064,244 B2 | 6/2006 | Jakobovits et al. |
| 7,067,475 B2 | 6/2006 | Cerretti et al. |
| 7,074,408 B2 | 7/2006 | Fanslow, III et al. |
| 7,087,225 B2 | 8/2006 | Yu et al. |
| 7,087,725 B2 | 8/2006 | Browning et al. |
| 7,109,298 B2 | 9/2006 | Browning et al. |
| 7,129,061 B1 | 10/2006 | Browning et al. |
| 7,169,387 B2 | 1/2007 | Rennert |
| 7,175,849 B2 | 2/2007 | Baum et al. |
| 7,208,151 B2 | 4/2007 | Browning et al. |
| 7,355,008 B2 | 4/2008 | Stavenhagen et al. |
| 7,368,531 B2 | 5/2008 | Rosen et al. |
| 7,482,430 B2 | 1/2009 | Wiley |
| 7,482,442 B2 | 1/2009 | Ruben et al. |
| 7,495,086 B2 | 2/2009 | Kim et al. |
| 7,498,304 B2 | 3/2009 | Kotkow et al. |
| 7,507,807 B2 | 3/2009 | Wiley |
| 7,517,962 B2 | 4/2009 | Wiley |
| 7,566,769 B2 | 7/2009 | Browning et al. |
| 7,579,001 B2 | 8/2009 | Rennert |
| 7,695,934 B2 | 4/2010 | Browning et al. |
| 7,731,963 B2 | 6/2010 | Browning et al. |
| 7,732,588 B2 | 6/2010 | Wiley |
| 7,754,884 B2 | 7/2010 | Bornhop et al. |
| 7,829,675 B2 | 11/2010 | Kim et al. |
| 8,048,422 B2 | 11/2011 | Burkly et al. |
| 8,048,635 B2 | 11/2011 | Burkly et al. |

(Continued)

FOREIGN PATENT DOCUMENTS

CA    2064710 A1    11/1991
EP    1354950 A1    10/2003

(Continued)

OTHER PUBLICATIONS

Chicheportiche et al., Arthritis Res., 2002, vol. 4:126-133.*
Ljung et al., Gut, 2004, vol. 53:849-853.*
Abbas, A.K. et al. (eds.), "General Properties of Immune Responses", in *Introduction to Immunology, Cellular and Molecular Immunology*. Philadelphia: WB Saunders Co., 1991; Chapter One, pp. 4-12.
Abbas, A.K. et al. (eds.), "Immunity to Microbes", in *Introduction to Immunology, Cellular and Molecular Immunology*. Philadelphia: WB Saunders Co., 1991; Chapter Fifteen, pp. 302-314.
Abreu-Martin et al., "Divergent Induction of Apoptosis and IL-8 Secretion in HT-29 Cells in Response to TNF-α and Ligation of Fas Antigen", *J. Immunol*. 155:4147-4154 (1995).

(Continued)

*Primary Examiner* — Xiaozhen Xie
(74) *Attorney, Agent, or Firm* — Finnegan, Henderson, Farabow, Garrett & Dunner, LLP

(57) ABSTRACT

Methods of treating inflammatory disorders, such as rheumatoid arthritis, by modulating TWEAK and TNF-α are disclosed, as are other methods.

26 Claims, 8 Drawing Sheets

(56) References Cited

U.S. PATENT DOCUMENTS

| | | |
|---|---|---|
| 2002/0004041 A1 | 1/2002 | Albert et al. |
| 2002/0010180 A1 | 1/2002 | Feldmann et al. |
| 2002/0015703 A1 | 2/2002 | Rennert |
| 2003/0148314 A1 | 8/2003 | Berger et al. |
| 2003/0170228 A1 | 9/2003 | Ashkenazi et al. |
| 2003/0198640 A1 | 10/2003 | Yu et al. |
| 2003/0211096 A1 | 11/2003 | Ashkenazi et al. |
| 2003/0216546 A1 | 11/2003 | Tykocinski et al. |
| 2004/0014176 A1 | 1/2004 | Ashkenzai et al. |
| 2004/0018170 A1 | 1/2004 | Shirwan |
| 2004/0033495 A1 | 2/2004 | Murray et al. |
| 2004/0038349 A1 | 2/2004 | Hilbert et al. |
| 2004/0047854 A1 | 3/2004 | Black et al. |
| 2004/0076955 A1 | 4/2004 | Mack et al. |
| 2004/0091473 A1 | 5/2004 | DuBose et al. |
| 2004/0175744 A1 | 9/2004 | Hu et al. |
| 2004/0176296 A1 | 9/2004 | Holtzman et al. |
| 2004/0203083 A1 | 10/2004 | Buechler et al. |
| 2005/0008625 A1 | 1/2005 | Balint et al. |
| 2005/0079574 A1 | 4/2005 | Bond |
| 2005/0181375 A1 | 8/2005 | Aziz et al. |
| 2005/0208500 A1 | 9/2005 | Erlander et al. |
| 2006/0003932 A1 | 1/2006 | Jakubowski et al. |
| 2006/0211090 A1 | 9/2006 | Bejanin et al. |
| 2006/0240004 A1 | 10/2006 | Burkly et al. |
| 2007/0280940 A1 | 12/2007 | Winkles et al. |
| 2008/0004432 A1 | 1/2008 | Ruben et al. |
| 2008/0187544 A1 | 8/2008 | Burkly et al. |
| 2008/0279853 A1 | 11/2008 | Burkly et al. |
| 2008/0286271 A1 | 11/2008 | Ashkenazi et al. |
| 2009/0068102 A1 | 3/2009 | Burkly et al. |
| 2009/0124993 A1 | 5/2009 | Burkly et al. |
| 2009/0148900 A1 | 6/2009 | Ruben et al. |
| 2009/0311313 A1 | 12/2009 | Burkly et al. |
| 2009/0324602 A1 | 12/2009 | Garber et al. |
| 2010/0061985 A1 | 3/2010 | Rennert |
| 2010/0183548 A1 | 7/2010 | Wiley |
| 2010/0260761 A1 | 10/2010 | Browning et al. |
| 2010/0272721 A1 | 10/2010 | Burkly et al. |
| 2010/0284933 A1 | 11/2010 | Burkly |
| 2011/0002924 A1 | 1/2011 | Browning et al. |
| 2012/0009178 A1 | 1/2012 | Burkly et al. |
| 2012/0015024 A1 | 1/2012 | Burkly et al. |
| 2012/0020913 A1 | 1/2012 | Burkly |
| 2012/0020970 A1 | 1/2012 | Burkly et al. |
| 2012/0027751 A1 | 2/2012 | Rennert |
| 2012/0121583 A1 | 5/2012 | Baehner et al. |
| 2012/0183542 A1 | 7/2012 | Burkly et al. |
| 2013/0095175 A1 | 4/2013 | Burkly et al. |

FOREIGN PATENT DOCUMENTS

| | | |
|---|---|---|
| EP | 1566636 A1 | 8/2005 |
| EP | 1721157 B1 | 4/2011 |
| JP | 5-501062 A | 3/1993 |
| JP | 2002-527096 A | 8/2002 |
| WO | WO 95/14772 A1 | 6/1995 |
| WO | WO 96/18725 A1 | 6/1996 |
| WO | WO 98/05783 A1 | 2/1998 |
| WO | WO 98/35061 A2 | 8/1998 |
| WO | WO 98/52976 A1 | 11/1998 |
| WO | WO 98/55508 A2 | 12/1998 |
| WO | WO 99/11791 A2 | 3/1999 |
| WO | WO 99/19490 A1 | 4/1999 |
| WO | WO 99/59614 A1 | 11/1999 |
| WO | WO 99/61471 A2 | 12/1999 |
| WO | WO 00/23459 A1 | 4/2000 |
| WO | WO 00/34317 A2 | 6/2000 |
| WO | WO 00/37638 A2 | 6/2000 |
| WO | WO 00/42073 A1 | 7/2000 |
| WO | WO 01/45730 A2 | 6/2001 |
| WO | WO 01/53486 A1 | 7/2001 |
| WO | WO 01/55112 A1 | 8/2001 |
| WO | WO 01/85193 A2 | 11/2001 |
| WO | WO 02/22166 A2 | 3/2002 |
| WO | WO 02/053737 A1 | 7/2002 |
| WO | WO 02/102994 A2 | 12/2002 |
| WO | WO 03/040307 A2 | 5/2003 |
| WO | WO 03/086311 A2 | 10/2003 |
| WO | WO 2004/074433 A2 | 9/2004 |
| WO | WO 2005/010045 A1 | 2/2005 |
| WO | WO 2005/080972 A1 | 9/2005 |
| WO | WO 2006/047172 A1 | 5/2006 |
| WO | WO 2006/052926 A2 | 5/2006 |
| WO | WO 2006/088890 A2 | 8/2006 |
| WO | WO 2006/089095 A2 | 8/2006 |
| WO | WO 2006/096487 A2 | 9/2006 |
| WO | WO 2006/122187 A2 | 11/2006 |
| WO | WO 2006/130374 A2 | 12/2006 |
| WO | WO 2006/130429 A2 | 12/2006 |
| WO | WO 2006/138219 A2 | 12/2006 |
| WO | WO 2008/048924 A2 | 4/2008 |
| WO | WO 2009/140177 A2 | 11/2009 |
| WO | WO 2010/085648 A2 | 7/2010 |
| WO | WO 2010/088534 A1 | 8/2010 |

OTHER PUBLICATIONS

Achiron et al., "Intravenus immunoglobulin treatment following the first demyelinating event suggestive of multiple sclerosis", *Arch. Neurol.* 61:1515-1520 (2004).

Agnello et al., "Increased peripheral benzodiazepine binding sites and pentraxin 3 expression in the spinal cord during EAE: relation to inflammatory cytokines and modulation by dexamethasone and rolipram" *J. Neuroimmunol.* 109:105-111 (2000).

Agrawal, "Antisense Oligonucleotides: Towards Clinical Trials", *TIBTECH* 14:376-387 (1996).

Akahori et al., "Immunoglobulin kappa light chain VLJ region [*Homo sapiens*]", NCBI database accession No. GI:21669075, GenBank Accession No. BAC01562 (Jun. 25, 2001).

Amakawa et al., "Impaired Negative Selection of T Cells in Hodgkin's Disease Antigen CD3O-Deficient Mice", *Cell* 84:551-562 (1996).

Amendola et al., "Altered sensorimotor development in a transgenic mouse model of amyotrophic lateral sclerosis", *Eur. J. Neurosci.* 20:2822-2826 (2004).

Anderson, "Human Gene Therapy", *Nature* 392:25-30 (1998).

Andrews et al., "Spontaneous Murine Lupus-like Syndromes", *J. Exp. Med.* 148:1198-1215 (1978).

Angal et al., "A single amino acid substitution abolishes the heterogeneity of chimeric mouse/human (IgG4) antibody", *Mol. Immunol.* 30:105-108 (1993).

Ashkenazi et al., "Death Receptors: Signaling and Modulation", *Science, New Series* 281(5381):1305-1308 (1998).

Bach-Elias et al., "Presence of autoantibodies against small nuclear ribonucleoprotein epitopes in Chagas' patients' sera", *Parasitol. Res.* 84:796-799 (1998).

Badley et al., "Upregulation of Fas Ligand Expression by Human Immunodeficiency Virus in Human Macrophages Mediates Apoptosis of Uninfected T Lymphocytes", *J. Virology* 70:199-206 (1996).

Banati et al., "The peripheral benzodiazepine binding site in the brain in multiple sclerosis", *Brain* 123:2321-2337 (2000).

Barrios et al., "Length of the antibody heavy chain complementarity determining region 3 as a specificity-determining factor", *J. Mol. Recog.* 17:332-338 (2004).

Bateller et al., "Liver fibrosis", *J. Clin. Invest.*, 115(2):209-218 (2005).

Bendele et al., "Combination Benefit of Treatment with the Cytokine Inhibitors Interleukin-1 Receptor Antagonist and PEGylated Soluble Tumor Necrosis Factor Receptor Type 1 in Animal Models of Rheumatoid Arthritis", *Arthritis Rheum.* 43(12):2648-2659 (2000).

Bodmer et al., "TRAMP, a Novel Apoptosis-Mediating Receptor with Sequence Homology to Tumor Necrosis Factor Receptor 1 and Fas(Apo-1/CD95)", *Immunity* 6:79-88 (1997).

Boor et al., "Treatment targets in renal fibrosis", *Nephrol. Dial. Transplant.* 22:3391-3407 (2007).

(56) References Cited

OTHER PUBLICATIONS

Bose et al., "Problems in using statistical analysis of replacement and silent mutations in antibody genes for determining antigen-driven affinity selection", *Immunology* 116:172-183 (2005).

Boucraut et al., "Anti-TWEAK Monoclonal Antibodies Reduce CNS Immune Cell Infiltration and Severity of Experimental Autoimmune Encephalomyelitis" *Aegean Conference Series, vol. 12: Autoimmunity: Mechanisms and Novel Treatments*. Myconos, Greece, Oct. 8-13, 2003; Abstract No. 64, p. 89.

Bowie et al., "Deciphering the Message in Protein Sequences: Tolerance to Amino Acid Substitutions", *Science* 247:1306-1310 (1990).

Branch, "A good antisense molecule is hard to find", *TIBS* 23:45-50 (1998).

Brojatsch et al., "CAR1, a TNFR-Related Protein, Is a Cellular Receptor for Cytopathic Avian Leukosis-Sarcoma Viruses and Mediates Apoptosis", *Cell* 87:845-855 (1996).

Brown et al., "The Fn14 cytoplasmic tail binds tumour-necrosis-factor-receptor-associated factors 1, 2, 3 and 5 and mediates nuclear factor-kappaB activation",*Biochem. J.* 371:395-403 (2003).

Browning et al., "Characterization of Surface Lymphotoxin Forms", *J. Immunol.* 154:33-46 (1995).

Browning et al., "Preparation and Characterization of Soluble Recombinant Heterotrimeric Complexes of Human Lymphotoxins Alpha and Beta", *J. Biol. Chem.* 271:8618-8626 (1996).

Browning et al., "Signaling through the Lymphotoxin Beta Receptor Induces the Death of Some Adenocarcinoma Tumor Lines", *J. Exp. Med.* 183:867-878 (1996).

Browning et al., "Studies on the Differing Effects of Tumor Necrosis Factor and Lymphotoxin on the Growth of Several Human Tumor Lines", *J. Immunol.* 143:1859-1867 (1989).

Browning, J., Second Declaration under 37 CFR 1.132 of Jeffrey Browning, Ph.D. from U.S. Appl. No. 09/245,198, Declaration filed on Jun. 27, 2005.

Buatois et al., "Pan-CC Chemokine Neutralization Restricts Splenocyte Egress and Reduces Inflammation in a Model of Arthritis",*J. Immunol.* 185:2544-2554 (2010).

Bucher et al., "A Generalized Profile Syntax for Biomolecular Sequence Motifs and Its Function in Automatic Sequence Interpretation", Proc. Second International Conference on Intelligent Systems for Molecular Biology. Altman, Brutlag, Karp, Lathrop, Searls (Eds.), pp. 53-61 (1994).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", *J. Cell. Biol.* 111:2129-2138 (1990).

Byrne et al., "An Antibody to IP-10 Is a Potent Antagonist of Cell Migration In Vitro and In Vivo and Does Not Affect Disease in Several Animal Models of Inflammation", *Autoimmunity* 42(3):171-182 (2009).

Campbell et al., "Proinflammatory Effects of TWEAK/Fn14 Interactions in Glomerular Mesangial Cells",*J. Immunol.* 176:1889-1898 (2006).

Campbell et al., "The Role of TWEAK/Fn14 in the Pathogenesis of Inflammation and Systemic Autoimmunity", *Frontiers Biosci.* 9:2273-2284 (2004).

Campbell, "The Role of TWEAK/Fn14 Interactions in Antibody Induced Glomerulonephritis", Dissertation, Albert Einstein College of Medicine, Yeshiva University, Nov. 2007. ProQuest, LLC, Ann Arbor, MI, 2009; UMI Microform No. 3340631.

Cassiano et al., "Molecular cloning of a novel receptor for TWEAK", *Scand. J. Immunol.* 51 (Suppl. 1):I-III (Abstract 2.2) (2000).

Castro et al., "Fas Modulation of Apoptosis during Negative Selection of Thymocytes" *Immunity* 6:617-627 (1996).

Chaplin et al., "Cytokine regulation of secondary lymphoid organ development", *Curr. Opin. Immunol.* 10:289-297 (1998).

Chicheportiche et al., "Down-Regulated Expression of TWEAK mRNA in Acute and Chronic Inflammatory Pathologies", *Biochem. Biophys. Res. Commun.* 279(1):162-165 (2000).

Chicheportiche et al., "Proinflammatory Activity of TWEAK on Human Dermal Fibroblasts and Synoviocytes: Blocking and Enhancing Effects of Anti-TWEAK Monoclonal Antibodies", *Arthritis Res.* 4(2):126-133 (2002). Epub Nov. 9, 2001.

Chicheportiche et al., "TWEAK, a new secreted ligand in the tumor necrosis factor family that weakly induces apoptosis",*J. Biol. Chem.* 272(51):32401-32410 (Dec. 19, 1997).

Chothia et al., "Structural repertoire of the human $V_H$ segments", *J. Mol. Biol.* 227:799-817 (1992).

Clackson et al., "Making antibody fragments using phage display libraries", *Nature* 352:624-628 (1991).

Clark et al., "Trends in antibody sequence changes during the somatic hypermutation process", *J. Immunol.* 177:333-340 (2006).

Comi et al. "European/Canadian multicenter, double-blind, randomized, placebo-controlled study of the effects of glatiramer acetate on magnetic resonance imaging-measured disease activity and burden in patients with relapsing multiple sclerosis", *Ann. Neurol.* 49: 290-297 (2001).

Consilvio et al. "Neuroinflammation, COX-2, and ALS—a dual role?", *Exper. Neurol.* 187:1-10 (2004).

Courtenay et al., "Immunisation against heterologous type II collagen induces arthritis in mice", *Nature* 283:666-668 (1980).

Culp et al. "Anti-TweakR antibodies inhibit tumor growth in vivo through dual mechanisms", *Proc. Annu. Mtg. Amer. Assoc. Cancer Res.* 49:354, Abstract 1511 (Apr. 16, 2008).

Cwirla et al., "Peptides on Phage: A Vast Library of Peptides for Identifying Ligands", *Proc. Natl. Acad. Sci. USA* 87:6378-6382 (1990).

Dallman, "Cytokines and transplantation: Th1/Th2 regulation of the immune response to solid organ transplants in the adult", *Curr. Opin. Immunol.* 7:632-638 (1995).

Darnay et al. ,"Signal Transduction by Tumor Necrosis Factor and Tumor Necrosis Related Ligands and Their Receptors", *Ann. Rheum. Dis.* 58(Suppl. 1):I2-I13 (1999).

David et al., "A study of the structural correlates of affinity maturation: Antibody affinity as a funcetion of chemical interactions, structural plasticity and stability", *Mol. Immunol.* 44:1342-1351 (2007).

Davies et al., "Single antibody domains as small recognition units: design and in vitro antigen selection of camelized, human VH domains with improved protein stability", *Protein Eng.* 9(6):531-537 (1996).

De Benedette et al., "Role of 4-1BB Ligand in Costimulation of T Lymphocyte Growth and its Upregulation on M12 B Lymphomas by cAMP", *J. Exp. Med.* 181:985-992 (1995).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody" *J. Immunol.* 169:3076-3084 (2002).

De Wit et al., "Preferential Activation of Th2 Cells in Chronic Graft-versus-Host Reaction", *J. Immunol.* 150(2):361-366 (1993).

Debruyne et al., "PET visualization of microglia in multiple sclerosis patients using [$^{11}$C]PK11195" *Eur. J. Neurol.* 10:257-264 (2003).

Degli-Esposti, "To die or not to die—the quest of the TRAIL receptors", *J. Leukocyte Biol.* 65:535-542 (1999).

Dermer, "Another Anniversary for the War on Cancer", *BioTechnology* 12:320 (1994).

Desplat-Jégo et al. "TWEAK is expressed at the cell surface of monocytes during multiple sclerosis", *J. Leukocyte Biol.* 85:132-135 (2009).

Desplat-Jégo et al., "Anti-TWEAK monoclonal antibodies reduce immune cell infiltration in the central nervous system and severity of experimental autoimmune encephalomyelitis", *Clin. Immunol.* 117(1):15-23 (2005).

Desplat-Jégo et al., "TWEAK Is Expressed by Glial Cells, Induces Astrocyte Proliferation and Increases EAE Severity", *J. Neuroimmunol.* 133:116-123 (2002).

Dias et al., "The Role of CXC Chemokines in the Regulation of Tumor Angiogenesis", *Cancer Invest.* 19:732-738 (2001).

(56) References Cited

OTHER PUBLICATIONS

Dohi et al., "TWEAK/Fn14 Pathway: A Nonredundant Role in Intestinal Damage in Mice Through a TWEAK/Intestinal Epithelial Cell Axis" *Gastroenterology* 136(3):912-923 (2009). EPub. Nov. 8, 2008.
Donahue et al., "TWEAK Is an Endothelial Cell Growth and Chemotactic Factor That Also Potentiates FGF-2 and VEGF-A Mitogenic Activity", *Arterioscler. Thromb. Vasc. Biol.* 23:594-600 (2003).
Durie et al., "Antibody to the Ligand of CD40, gp39, Blocks the Occurrence of the Acute and Chronic Forms of Graft-vs-Host Disease", *J. Clin. Invest.* 94:1333-1338 (1994).
Eck et al., "The Structure of Human Lymphotoxin (Tumor Necrosis Factor-Beta) at 1.9-Å Resolution", *J. Biol. Chem.* 267:2119-2122 (1992).
European Patent Application No. 03721647: Supplementary Partial Search Report, dated Aug. 9, 2005.
European Patent Application No. 06759489: Extended Search Report, including Search Opinion and Supplementary Search Report, dated Jul. 31, 2009.
European Patent Application No. 06760258: Extended Search Report, including Search Opinion and Supplementary Search Report, dated Jun. 19, 2009.
European Patent Application No. 08104327: Extended Search Report, including Search Opinion, dated Feb. 6, 2009.
European Patent Application No. 10181803: Extended Search Report, including Search Opinion, dated Jul. 6, 2012.
European Patent Application No. 10181803: Partial Search Report, dated Mar. 19, 2012.
European Patent Application No. 10181810: Extended Search Report, including Search Opinion, dated Jul. 6, 2012.
European Patent Application No. 10181810: Partial Search Report, dated Mar. 19, 2012.
Falk et al., "Expression of the APO-1 Antigen in Burkitt Lymphoma Cell Lines Correlates with a Shift Towards a Lymphoblastoid Phenotype", *Blood* 79:3300-3306 (1992).
Feng et al., "The Fn14 Immediate-Early Response Gene Is Induced During Liver Regeneration and Highly Expressed in Both Human and Murine Hepatocellular Carcinomas", *Am. J. Pathol.* 156(4):1253-1261 (2000).
Flynn et al., "CD4 T Cell Cytokine Differentiation: The B Cell Activation Molecule, OX40 Ligand, Instructs CD4 T Cells to Express Interleukin 4 and Upregulates Expression of the Chemokine Receptor, Blr-1", *J. Exp. Med.* 188:297-304 (1998).
Fox, D., "Biological Therapies: A Novel Approach to the Treatment of Autoimmune Disease", *Am. J. Med.* 99:82-88 (1995).
Fujimoto et al., "Interleukin-6 Blockade Suppresses Autoimmune Arthritis in Mice by the Inhibition of Inflammatory Th17 Responses", *Arthritis & Rheumatism* 58:3710-3719 (2008).
Funakoshi et al., "Inhibition of Human BOCell Lymphoma Growth by CD40 Stimulation", *Blood* 83:2787-2794 (1994).
Galle et al., "Involvement of the CD95 (APO-1/Fas) Receptor and Ligand in Liver Damage", *J. Exp. Med.* 182:1223-1230 (1995).
Games et al., "Alzheimer-type neuropathology in transgenic mice overexpressing V717F beta-amyloid precursor protein", *Nature* 373:523-527 (1995).
Gauchat et al., "Human CD40-Ligand: Molecular Cloning, Cellular Distribution and Regulation of Expression by Factors Controlling IgE Production", *FEBS Lett.* 315:259-266 (1993).
Gavish et al., "Enigma of the Peripheral Benzodiazepine Receptor", *Pharmacological Reviews* 51(4):629-650 (1999).
GENBANK Acc. No. AAB49141, "Anti-DNA immunoglobulin heavy chain IgG [*Mus musculus*]" (1996).
GENETECH, Inc., Full Prescribing Information for Actrema (Jan. 2010) (24 pages).
Gilgun-Sherki et al., "Analysis of Gene Expression in MOG-Induced Experimental Autoimmune Encephalomyelitis After Treatment with a Novel Brain-Penetrating Antioxidant" *J. Mol. Neurosci.* 27(1):125-136 (2005).

Gleichmann et al., "A systemic lupus erythematosus (SLE)-like disease in mice induced by abnormal T-B cell cooperation. Preferential formation of autoantibodies characteristic of SLE", *Eur. J. Immunol.* 12:152-159 (1982).
Grewal et al., "The CD40 Ligand. At the Center of the Immune Universe?", *Immunol. Res.* 16:59-70 (1997).
Grewal et al., "The Role of CD40 Ligand in Costimulation and T-Cell Activation", *Immunol. Rev.* 153:85-106 (1996).
Gruss et al., "Pleiotrophic Effects of the CD30 Ligand on CD30-Expressing Cells and Lymphoma Cell Lines", *Blood* 83:2045-2056 (1994).
Gruss et al., "Tumor Necrosis Factor Ligand Superfamily: Involvement in the Pathology of Malignant Lymphomas" *Blood* 85:3378-3404 (1995).
Hahm et al., "Tweak overexpression induces hyperplasia in liver and kidney", *FASEB J.* 17(4-5):Abstract No. 471.5 (2003).
Han et al., "Identification of Differentially Expressed Genes in Pancreatic Cancer Cells Using cDNA Microarray", *Cancer Research* 62:2890-2896 (May 15, 2002).
Han et al., "Overexpression of FN14/Teak receptor in pancreatic cancer", *Proc. Am. Assoc. Cancer Res. Annual Meeting* 46(Suppl. S):Abstract No. 2363 (Apr. 18, 2005).
Hess et al., "A Novel Function of CD40: Induction of Cell Death in Transformed Cells", *J. Exp. Med.* 183:159-167 (1996).
Hillier et al., "The Wash U-Merck EST project yy19a08.s1 *Homo sapiens* cDNA clone 271670 3", EMBL Database Entry HS070272, Accesion No. N35070 (Jan. 19, 1996).
Hillier et al., "The WashU-Merck EST project yyl9a08.s1 *Homo sapiens* cDNA clone 154742 5", EMBL Database Entry HS379117, Accession No. R55379 (May 28, 1995).
Ho et al., "Soluble Tumor Necrosis Factor-Like Weak Inducer of Apoptosis Overexpression in HEK293 Cells Promotes Tumor Growth and Angiogenesis in Athymic Nude Mice", *Cancer Research* 64:8968-8972 (Dec. 15, 2004).
Ibrahim et al., "Gene Expression Profiling of the Nervous System in Murine Experimental Autoimmune Encephalomyelitis" *Brain* 124(10):1927-1938 (2001).
Ike et al., "Solid Phase Synthesis of Polynucleotides. VIII. Synthesis of Mixed Oligodeoxyribonucleotides by the Phosphotriester Solid Phase Method", *Nucl. Acids Res.* 11:477-488 (1983).
International Preliminary Examination Report issued in International Patent Application No. PCT/US03/11350; Date of Mailing: Nov. 23, 2004.
International Search Report and Written Opinion issued in International Patent Application No. PCT/US06/005217; Date of Mailing: Aug. 4, 2006.
International Search Report and Written Opinion issued in International Patent Application No. PCT/US06/05597; Date of Mailing: May 21, 2008.
International Search Report and Written Opinion issued in International Patent Application No. PCT/US06/108077; Date of Mailing: Jul. 16, 2008.
International Search Report and Written Opinion issued in International Patent Application No. PCT/US06/19706; Date of Mailing: Oct. 9, 2007.
International Search Report and Written Opinion issued in International Patent Application No. PCT/US06/022830; Date of Mailing: Jan. 26, 2007.
International Search Report and Written Opinion issued in International Patent Application No. PCT/US07/81374; Date of Mailing: Mar. 17, 2008.
International Search Report issued in International Patent Application No. PCT/US00/01044; Date of Mailing: Jun. 6, 2000.
International Search Report issued in International Patent Application No. PCT/US03/11350; Date of Mailing: Mar. 10, 2004.
Iwasaki et al., "Cotreatment of amyotrophic lateral sclerosis patients", *Rinsho Shinkeigaku* 39:1253-1255 (1999) (Abstract).
Jain et al., "A Novel Role for Tumor Necrosis Factor Like Weak Inducer of Apoptosis (TWEAK) in the Development of Cardiac Dysfunction and Failure", *Circulation* 119:2058-2068, with supplemental material (2009).
Jakubowski et al., "Dual role for TWEAK in angiogenic regulation", *J. Cell Sci.* 115(Pt. 2):267-274 (Jan. 15, 2002).

(56) References Cited

OTHER PUBLICATIONS

Jakubowski et al., "TWEAK induces liver progenitor cell proliferation", *J. Clin. Invest.* 115(9):2330-2340 (Sep. 2005).
Jakubowski et al., "TWEAK Synergizes with Basis Fibroblast Growth Factor to Induce Endothelial Cell Proliferation, Migration and Lumen Morphogenesis", *Scand. J. Immunol.* 51(Suppl. 1):62, Abstract 1.30 (2000).
Japanese Office Action issued in Japanese Patent Application No. 2008-511317, mailed Nov. 28, 2011.
Juengst, "What next for human gene therapy", *BMJ* 326:1410-1411 (2003).
Kaduka et al., "TWEAK Mediates Anti-Tumor Effect of Tumor-Infiltrating Macrophage", *Biochem. Biophys. Res. Commun.* 331:384-390 (2005).
Kalled et al., "Anti-CD40 Ligand Antibody Treatment of $SNF_1$ Mice with Established Nephritis: Preservation of Kidney Function", *J. Immunol.* 160:2158-2165 (1998).
Kamata et al., "Involvement of TNF-Like Weak Inducer of Apoptosis in the Pathogenesis of Collagaen-Induced Arthritis" *J. Immunol.* 177:6433-6439 (2006).
Kang et al., "The Influence of a Polymorphism at Position -857 of the Tumour Necrosis Factor Alpha Gene on Clinical Response to Etanercept Therapy in Rheumatoid Arthritis", *Rheumatology* 44(4):547-552 (2005).
Kaplan et al., "Th2 Lymphocytes Kill Antigen Presenting Macrophages Through a TWEAK Dependant Pathway", *J. Invest. Med.* 46(7):287A (1998).
Kaplan et al., "The Apoptotic Ligands TRAIL, TWEAK, and Fas Ligand Mediate Monocyte Death Induced by Autologous Lupus T Cells", *J. Immunol.* 169:6020-6029 (2002).
Kaplan et al., "TRAIL (Apo2 Ligand) and TWEAK (Apo3 Ligand) Mediate $CD4^+$ T Cell Killing of Antigen-Presenting Macrophages", *J. Immunol.* 164:2897-2904 (2000).
Katsikis et al., "Fos Antigen Stimulation Induces Marked Apoptosis of T Lymphocytes in Human Immunodeficiency Virus-infected Individuals", *J. Exp. Med.* 181:2029-2036 (1995).
Kawabata et al., "Kansetsu ryumachi no aratana yakubutsu ryouhou heno tenbou", *Yakuji* 47(3):49-53 (2005) (Japanese).
Kawakita et al., "Functional expression of TWEAK in human hepatocellular carcinoma: possible implication in cell proliferation and tumor angiogenesis", *Biochem. Biophys. Res. Commun.* 318:726-733 (2004).
Kirk et al., "CTLA4-Ig and anti-CD40 ligand prevent renal allograft rejection in primates", *Proc. Natl. Acad. Sci. USA* 94:8789-8794 (1997).
Knappik et al., "Fully Synthetic Human Combinatorial Antibody Libraries (HuCAL) Based on Modular Consensus Frameworks and CDRs Randomized with Trinucleotides", *J. Mol. Biol.* 296(1):57-86 (2000).
Kobrin et al., "A V region mutation in a phosphocholine-binding monoclonal antibody results in loss of antigen binding", *J. Immunol.* 146:2017-2020 (1991).
Kornek et al., "Multiple Sclerosis and Chronic Autoimmune Encephalomyelitis. A Comparative Quantitative Study of Axonal Injury in Active, Inactive, and Remyelinated Lesions", *Am. J. Pathol.* 157(1):267-276 (2000).
Krenger et al., "Graft-versus-Host Disease and the Th1/Th2 Paradigm", *Immunol. Res.* 15:50-73 (1996).
Kuhn et al., "A mouse model of graded contusive spinal cord injury", *J. Neurotrauma* 15:125-140 (1998).
Kurtzke, J.F., "Clinical Definition for Multiple Sclerosis Treatment Trials", *Ann. Neurol.* 36:S73-S79 (1994).
Kurtzke, J.F., "Rating neurologic impairment in multiple sclerosis: an expanded disability status scale (EDSS)", *Neurology* 33:1444-1452 (1983).
Lee et al., "T Cell Receptor-dependent Cell Death of T Cell Hybridomas Mediated by the CD30 Cytoplasmic Domain in Association with Tumor Necrosis Factor Receptor-Associated Factors", *J. Exp. Med.* 183:669-674 (1996).

Lennon et al., "The I.M.A.G.E. Consortium: An Integrated Molecular Analysis of Genomes and Their Expression", *Genomics* 33:151-152 (Apr. 1996).
Lenschow et al., "Differential Effects of Anti-B7-1 and Anti-B7-2 Monoclonal Antibody Treatment on the Development of Diabetes in the Nonobese Diabetic Mouse", *J. Exp. Med.* 181:1145-1155 (1995).
Lin et al., "Very late antigen 4 (VLA4) antagonists as anti-inflammatory agents", *Curr. Opin. Chem. Biol.* 2:453-457 (1998).
Lund et al., "Human FcγRI and FcγRII interact with distinct but overlapping sites on human IgG", *J. Immunol.* 147:2657-2662 (1991).
Lynch et al., "TWEAK Induces Angiogenesis and Proliferation of Endothelial Cells", *J. Biol. Chem.* 274(13):8455-8459 (1999).
Lynch et al., "TWEAK Induces Proliferation in Endothelial Cells and Substitutes for EGF and Hydrocortisone in Culture", *J. Interferon Cytokine Res.* 18:A-46, Abstract 2.16 (1998).
MacKay et al., "Turning off follicular dendritic cells", *Nature* 395:26-27 (1998).
Marra et al., "The WashU-HHMI Mouse EST project. my18d09.r1 Barstead mouse heart MPLRB3 Mus musculus cDNA clone 696209 5". GenBank Database Accession No. AA221610 (Feb. 15, 1997).
Marsters et al., "Identification of a ligand for the death-domain-containing receptor Apo3", *Current Biology* 8:525-528 (1998).
Martin-Villalba et al., "Therapeutic Neutralization of CD-95-Ligand and TNF Attenuates Brain Damage in Stroke", *Cell Death Diff.* 8:679-686 (2001).
Masliah et al., "Dopaminergic Loss and Inclusion Body Formation in α-Synuclein Mice: Implications for Neurodegenerative Disorders", *Science* 287:1265-1269 (2000).
Mattner et al. "Evaluation of radiolabelled peripheral benzodiazepine receptor ligand in the central nervous system inflammation of experimental autoimmune encephalomyelitis: a possible role for imaging multiple sclerosis", *Eur. J. Nucl. Med. Mol. Imaging* 32: 557-563 (2005).
Mattson et al., "NF-κb in neuronal plasticity and neurodegenerative disorders", *J. Clin. Invest.* 107:247-254 (2001).
Meighan-Mantha et al., "The Mitogen-inducible *Fn14* Gene Encodes a Type I Transmembrane Protein that Modulates Fibroblast Adhesion and Migration", *J. Biol. Chem.* 274(46):33166-33176 (Nov. 12, 1999).
Michaelson et al., "Tweak induces mammary epithelial branching morphogenesis", *Oncogene* 24:2613-2624 (2005).
Miller et al., "Genetic Studies of the *lac* Repressor. IX. Generation of Altered Proteins by the Suppression of Nonsense Mutations", *J. Mol. Biol.* 131:191-222 (1979).
Miller et al., "Riluzole for amyotrophic lateral Sclerosis (AS)/motor neuron disease (MND)", *Cochrane Database Syst Rev.*, Issue 2. Art. No. CD001447, pp. 1-25 (2002).
Mohan et al., "Interaction Between CD40 and Its Ligand gp39 in the Development of Murine Lupus Nephritis", *J. Immunol.* 154:1470-1480 (1995).
Montgomery et al., "Herpes Simplex Virus-1 Entry into Cells Mediated by a Novel Member of the TNF/NGF Receptor Family", *Cell* 87:427-436 (1996).
Morgan et al., "The N-terminal end of the $C_H2$ domain of chimeric human IgG1 anti-HLA-DR is necessary for C1q, FcγRI and FγRIII binding", *Immunology* 86:319-324 (1995).
Morris et al., "Experimental Induction of Systemic *Lupus erythematosus* By Recognition of Foreign Ia", *Clin. Immunol. Immunopathol.* 57:263-273 (1990).
Mueller et al., "Targeting fibroblast growth-factor-inducible-14 signaling protects from chronic relapsing experimental autoimmune encephalomyelitis", *J. Neuroimmunol.* 159(1-2):55-65 (2005).
Nagata, S., "Apoptosis by Death Factor" *Cell* 88:355-365 (1997).
Nakaya et al., "Regulation of Asialoglycoprotein Receptor Synthesis by Inflammation-Related Cytokines in HepG2 Cells", *J. Gastroenterol.* 29:24-30 (1994).
Nakayama et al., "Characterization of murine TWEAK and its receptor (Fn14) by monoclonal antibodies", *Biochem. Biophys. Res. Commun.* 306(4):819-825 (2003).
Nakayama et al., "Fibroblast Growth Factor-Inducible 14 Mediates Multiple Pathways of TWEAK-Induced Cell Death", *J. Immunol.* 170:341-348 (2003).

(56) References Cited

OTHER PUBLICATIONS

Nakayama et al., "Involvement of TWEAK in Interferon γ-stimulated Monocyte Cytotoxicicity", *J. Exp. Med.* 192(9):1373-1379 (2000).

Nakayama et al., "Multiple Pathways of Tweak-Induced Cell Death", *J. Immunol.* 168:734-743 (2002).

Neutra et al., "Intestinal Epithelium: A Model System for Study of Cell Differentiation and Polarized Cell Functions", in *Functional Epithelia Cells in Culture*. Liss (ed.), 1989; pp. 363-398.

Ngo et al., in *The Protein Folding Problem and Tertiary Structure Prediction*. K. Merz Jr. and S. Legrand (Eds.) Birkhauser, Boston, 1994; pp. 433 and 492-495.

Orkin et al., Report and Recommendations of the Panel to Assess the NIH Investment in Research on Gene Therapy (Dec. 7, 1995).

Patent Interference No. 105,513, Paper 106, Memorandum Opinion and Order, Decision on Motions.

Patent Interference No. 105,513, Paper 107, Decision—Bd. R. 125, Decision on Browning Misc. Motion 4 for Sanctions.

Patent Interference No. 105,513, Paper 108, Judgement, Preliminary Motions—Bd. R. 127.

Paul, "Fv Structure and Diversity in Three Dimensions", in *Fundamental Immunology*, 3rd. edition. New York: Raven Press, 1993; pp. 292-295.

Pepper et al., "Biphasic effect of transforming growth factor-$B_1$ on in vitro angiogenesis", *Exp. Cell Res.* 204(2):356-363 (Feb. 1993).

Perper et al., "TWEAK is a novel arthritogenic mediator", *J. Immunol.* 177(4):2610-2620 (Aug. 15, 2006).

Pitti et al., "Induction of Apoptosis by Apo-2 Ligand, a New Member of the Tumor Necrosis Factor Cytokine Family", *J. Biol. Chem.* 271:12687-12690 (1996).

Plowman et al., "Human Tumor Xenograft Models in NCI Drug Development", in *Anticancer Drug Development Guide: Preclinical Screening, Clinical Trials and Approval*. B. Teicher (ed.), Humana Press Inc., Totown, 1997; pp. 101-125.

Portanova et al., "Lupus-like autoimmunity in murine graft-versus-host disease", *Concepts Immunopathol.* 6:119-140 (1988).

Portolano et al., "Lack of promiscuity in autoantigen-specific H and L chain combinations as revealed by human H and L chain 'Roulette'" *J. Immunol.* 150(3):880-887 (1993).

Poser et al., "New Diagnostic Criteria for Multiple Sclerosis: Guidelines for Research Protocols", *Ann. Neurol.* 13:227-231 (1983).

Potrovita et al., "Tumor Necrosis Factor-Like Weak Inducer of Apoptosis-Induced Neurodegeneration", *J. Neurosci.* 24(38):8237-8244 (Sep. 22, 2004).

Potrovita et al., "'TWEAK—A Regulator of Neuronal Cell Death", *Naunyn-Schmiedeberg's Archives of Pharmacology* 369(Suppl. 1):R12, Abstr. 48 (Mar. 9, 2004).

Putterman et al., "Tweak Blockade Improves Kidney Disease in Lupus-Prone Mice: A Novel Approach to the Treatment of Lupus Nephritis?", Annual Meeting of Professional Research Scientists, Washington, D.C., Apr. 17-21, 2004. *FASEB J.*, 18(5), Experimental Biology 2004, Abstracts Part II:A839, Abstract No. 562.27 (2004).

Rizvi et al. "Current approved options for treating patients with multiple sclerosis", *Neurol.* 63 (Suppl .6): S8-S14 (2004).

Roberts et al., "Directed Evolution of a Protein: Selection of a Potent Neutrophil Elastase Inhibitors Displayed on M13 Fusion Phage", *Proc. Natl. Acad. Sci. USA* 89:2429-2433 (1992).

Romano et al., "Latest developments in gene transfer technology: achievements, perspectives, and controversies over therapeutic applications", *Stem Cells* 18:19-39 (2000).

Rosenberg et al., "Gene therapist, heal thyself", *Science* 287:1751 (2000).

Rovin et al., "Urine chemokines as biomarkers of human systemic lupus erythematosus activity", *J. Am. Soc. Nephrol.* 16:467-473 (2005).

Rubinsztein, "Lessons from animal models of Huntington's disease", *Trends Genet.* 18:202-209 (2002).

Rudikoff et al., "Single amino acid substitution altering antigen-binding specificity", *Proc. Natl. Acad. Sci. USA*, 79(6):1979-1983 (1982).

Rudinger, "Characteristics of the amino acids as components of a peptide hormone sequence", in *Peptide Hormones*. J.A. Parsons (Ed.), University Park Press, Baltimore, MD, 1976; pp. 1 and 6 (1976).

Ruuls et al., "The Length of Treatment Determines Whether IFN-Beta Prevents or Aggravates Experimental Autoimmune Encephalomyelitis in Lewis Rats", *J. Immunol.* 157:5721-5731 (1996).

Saas et al., "TWEAK Stimulation of Astrocytes and the Proinflammatory Consequences", *GLIA* 32(1):102-107 (2000).

Saemann et al., "Urinary tract infection in renal transplant recipients" *Eur. J. Clin. Invest.* 38(Suppl. 2):58-65 (2008).

Scamurra et al., "Ig heavy chain variable region VH3 family [*Homo sapiens*]", NCBI database Accession No. GI:33318898, GenBank Accession No. AAQ05352 (2002).

Schneider et al., "TWEAK Can Induce Cell Death via Endogenous TNF and TNF Receptor 1", *Eur. J. Immunol.* 29(6):1785-1792 (1999).

Semov et al., "Alterations in TNF- and IL-related Gene Expression in Space-flown WI38 Human Fibroblasts", *FASEB J.* 16(8):899-901 (2002).

Sharp et al., "The effect of peripheral nerve injury on disease progression in the SOD$^{1(G93A)}$ mouse model of amyotrophic lateral sclerosis", *Neuroscience* 130:897-910 (2005).

Shepard et al., "Monoclonal Antibody Therapy of Human Cancer: Taking the HER2 Protooncogene to the Clinic", *J. Clin. Immunol.* 11:117-127 (1991).

Smith et al., "CD30 Antigen, a Marker for Hodgkin's Lymphoma, Is a Receptor Whose Ligand Defines an Emerging Family of Cytokines with Homology to TNF", *Cell* 73:1349-1360 (1993).

Smith, M.D., "Etanercept Treatment of Rheumatoid Arthritis in the 'Real World'", *Ann. Rheum. Dis.* 62(1):95-96 (2003).

Sobel et al., "The Immunopathology of Experimental Allergic Encephalomyelitis", *J. Immunol.* 132:2393-2401 (1984).

Somia et al., "Gene therapy: trials and tribulations", *Nature Reviews Genetics* 1:91-99 (2000).

Song et al., "A single amino acid change (Asp 53 → Ala53) converts Survivin from anti-apoptotic to pro-apoptotic", *Mol. Biol. Cell* 15:1287-1296 (Mar. 2004).

Steinman et al., "Virtues and Pitfalls of EAE for the Development of Therapies for Multiple Sclerosis", *Trends Immunol.* 26(11):565-571 (2005).

Steinman, L., "Optic Neuritis, a New Variant of Experimental Encephalomyelitis, a Durable Model for All Seasons, Now in Its Seventieth Year", *J. Exp. Med.* 197(9):1065-1071 (2003).

Storkebaum et al., "Treatment of motoneuron degeneration by intracerebroventricular delivery of VEGF in a rat model of ALS", *Nat. Neurosci.* 8:85-92 (2005).

Stryer et al., in *Biochemistry*, 3rd Ed., W.H. Freeman and Co.: New York, 1988; pp. 31-33.

Stuber et al., "The T Cell-B Cell Interaction via OX40-OX40L Is Necessary for the T Cell-dependent Humoral Immune Response", *J. Exp. Med.* 183:979-989 (1996).

Sytwu et al., "The Roles of Fas/APO-1 (CD95) and TNF in Antigen-Induced Programmed Cell Death in T Cell Receptor Transgenic Mice", *Immunity* 5:17-30 (1996).

Takagi et al, "Blockage of Interleukin-6 Receptor Ameliorates Joint Disease in Murine Collagen-Induced Arthritis", *Arthritis & Rheumatism* 41:2117-2121 (1998).

Tanabe et al., "Fibroblast growth factor-inducible-14 is induced in axotomized neurons and promotes neurite outgrowth", *J. Neurosci.* 23:9675-9686 (2003).

Tannenbaum et al., "The CXC Chemokines IP-10 and Mig are Necessary for IL-12-Mediated Regression of the Mouse RENCA Tumor", *J. Immunol.* 161:927-932 (1998).

Tartaglia et al., "The Two Different Receptors for Tumor Necrosis Factor Mediate Distinct Cellular Responses", *Proc. Natl. Acad. Sci. USA* 88:9292-9296 (1991).

Techman, A., "Biogen Idec and University of Adelaide Find TWEAK Is a Novel Arthritogenic Mediator; Potential New Pathway in Rheumatoid Arthritis and Osteoarthritis Disease Process" *Musckuloskeletal Report*, Aug. 16, 2006, pp. 1-2 [online]. Retrieved from the Internet, www.mskreport.com, Aug. 2, 2010.

(56) References Cited

OTHER PUBLICATIONS

Teng et al., "Functional recovery following traumatic spinal cord injury mediated by a unique polymer scaffold seeded with neural stem cells", *PNAS* 99:3024-3029 (2002).
Theien et al., "Discordant effects of anti-VLA-4 treatment before and after onset of relapsing experimental autoimmune encephalomyelitis", *J. Clin. Invest.* 107:995-1006 (2001).
Tibbetts et al., "Cardiac Antigen-Specific Autoantibody Production Is Associated with Cardiomyopathy in *Trypanosoma cruzi*-Infected Mice", *J. Immunol.*152:1493-1499 (1994).
Tomlinson et al., "The repertoire of human germline $V_H$ sequences reveals about fifty groups of $V_H$ segments with different hypervariable loops", *J. Mol. Biol.* 227:776-798 (1992).
Tomlinson et al., "The structural repertoire of the human Vκ domain" *EMBO J.* 14:4628-4638 (1995).
Toogood et al., "The Immune Response Following Small Bowel Transplantation", *Transplantation* 62(6):851-855 (1996).
Tozawa et al., "Atarashii TNF Sogaizai (New TNF inhibitor)" *G.I. Research* 13(1):25-33 (2005) (Japanese).
Tran et al., "The Human Fn14 Receptor Gene Is Up-Regulated in Migrating Glioma Cells in Vitro and Overexpressed in Advanced Glial Tumors", Am. J. Pathol. 162(4):1313-1321 (Apr. 2003).
Tran et al., "The Tumor Necrosis Factor-like Weak Inducer of Apoptosis (TWEAK)-Fibroblast Growth Factor-inducible 14 (Fn14) Signaling System Regulates Glioma Cell Survival via NFκB Pathway Activation and $BCL-X_L$/BCL-W Expression", *J. Biol. Chem.* 280(5):3483-3492 (Feb. 4, 2005).
Traugott, "Detailed Analysis of Early Immunopathologic Events during Lesion Formation in Acute Experimental Autoimmune Encephalomyelitis", *Cell Immunol.* 119:114-129 (1989).
Trauth et al., "Monoclonal Anitbody-Mediated Tumor Regression by Induction of Apoptosis", *Science* 245:301-305 (1989).
Trentham et al., "Autoimmunity to Type II Collagen: An Experimental Model of Arthritis", *J. Exp. Med.* 146:857-868 (1977).
Tuohy et al., "A Synthetic Peptide from Myelin Proteolipid Protein Induces Experimental Allergic Encephalomyelitis", *J. Immunol.* 141:1126-1130 (1988).
U.S. Appl. No. 09/169,104 by Ashkenazi et al., filed Oct. 9, 1998.
U.S. Appl. No. 12/506,006 by Rennert: Non-Final Office Action, mailed Aug. 9, 2010.
Uchiyama et al., "Tocilizumab, a Humanized Anti-interleukin-6 Receptor Antibody, Ameliorates Joint Swelling in Established Monkey Collagen-Induced Arthritis", *Biol. Pharm. Bull.* 31(6):1159-1163 (2008).
Veenman et al., "Peripheral-type benzodiazepine receptors: their implication in brain disease", *Drug Dev. Res.* 50:355-370 (2000).
Verma et al., "Gene therapy—promises, problems and prospect", *Nature* 18:239-242 (1997).
Via "Advances in lupus stemming from the parent-into-F1 model", *Trends Immunol.* 31:236-245 (2010).
Via et al., "Role of cytotoxic T lymphocytes in the prevention of lupus-like disease occurring in a murine model of graft-vs-host disease", *J. Immunol.* 139:1840-1849 (1987).
Vowinckel et al. "PK11195 binding to the peripheral benzodiazepine receptor as a marker of microglia activation in multiple sclerosis and experimental autoimmune encephalomyelitis", *J. Neurosci. Res.* 50:345-353 (1997).
Wada et al., "Detection of urinary interleukin-8 in glomerular diseases" *Kidney International* 46:455-460 (1994).
Wamil et al., "CM101-mediated recovery of walking ability in adult mice paralyzed by spinal cord injury", *Proc. Natl. Acad. Sci. USA* 95:13188-13193 (1998).
Ward et al., "Blocking of adhesion molecules in vivo as anti-inflammatory therapy", *Ther. Immunol.* 1(3):165-171 (1994).
*Webster's II New Riverside University Dictionary*, "Preventing", Boston, Mass.: Houghton Mifflin Co., 1994; p. 933.
Wiley et al., "A Novel TNF Receptor Family Member Binds TWEAK and Is Implicated in Angiogenesis", *Immunity* 15:837-846 (2001).
Wiley et al., "Identification and Characterization of a New Member of the TNF Family that Induces Apoptosis", *Immunity* 3:673-682 (1995).
Wiley et al., "TWEAK, a member of the TNF superfamily, is a multifunctional cytokine that binds the TweakR/Fn14 receptor", *Cytokine & Growth Factor Reviews* 14:241-249 (2003).
Williams et al., "Anti-tumor necrosis factor ameliorates joint disease in murine collagen-induced arthritis" *Proc. Natl. Acad. Sci. USA* 89:9784-9788 (1992).
Williamson et al., "IL-12 Is a Central Mediator of Acute Graft-Versus-Host Disease in Mice", *J. Immunol.* 157(2):689-699 (1996).
Winkles et al., "Role of TWEAK and Fn14 in tumor biology", *Frontiers in Bioscience* 12:2761-2771 (Jan. 1, 2007).
Winkles et al., "TWEAK and Fn14: New molecular targets for cancer therapy?", *Cancer Letters* 235:11-17 (2006).
Wolinsky, J.S. "Glatiramer acetate for the treatment of multiple sclerosis", *Expert Opin. Pharmacother.* 5(4):875-891 (2004).
Written Opinion issued in International Patent Application No. PCT/US00/01044; Date of Mailing: Oct. 30, 2000.
Wuthrich et al., "Autoimmune tubulointerstitial nephritis: insight from experimental models", *Exp. Nephrol.* 6(4):288-293 (1998).
Yepes et al., "A Soluble Fn14-Fc Decoy Receptor Reduces Infarct Volume in a Murine Model of Cerebral Ischemia", *Am. J. Pathol.* 166:511-520 (2005).
Yonehara et al., "A Cell-Killing Monoclonal Antibody (ANTI-Fas) to a Cell Surface Antigen Co-Downregulated with the Receptor of Tumor Necrosis Factor", *J. Exp. Med.* 169:1747-1756 (1989).
Zhang et al., "TWEAK-Fn14 pathway inhibition protects the integrity of the neurovascular unit during cerebral ischemia", *J. Cerebral Blood Flow & Metab.* 27:534-544 (2007).
Zhao et al., "Different Gene Expression Patterns in Invasive Lobular and Ductal Carcinomas of the Breast", *Mol. Biol. Cell* 15:2523-2536 (Jun. 2004).
Zhao et al., "TWEAK/Fn14 Interactions Are Instrumental in the Pathogenesis of Nephritis in the Chronic Graft-versus-Host Model of Systemic Lupus Erythematosis", *J. Immunol.* 179:7949-7958 (2007).
Zheng et al., "Post-ischemic inflammation: molecular mechanisms and therapeutic implications", *Neurol. Res.*, 26:884-892 (2004), Abstract only.
Zhu et al., "Inhibition of tumor growth and metastasis by targeting tumor-associated angiogenesis with antagonists to the receptors of vascular endothelial growth factor", *Investigational New Drugs* 17:195-212 (1999).
Zohar et al., "Closed-head minimal traumatic brain injury produces long-term cognitive deficits in mice", *Neuroscience* 118:949-955 (2003).
[No Authors Listed], "Abetimus: Abetimus sodium, LJP 394", *BioDrugs* 17(3):212-215 (2003) (Abstract only).
Alarcón-Segovia at al., "LJP 394 for the Prevention of Renal Flare in Patients With Systemic Lupus Erythematosus", *Arthritis & Rheumatism* 48(2):442-454 (2003).
Burkly et al., "TWEAKing tissue remodeling by a multifunctional cytokine: Role of TWEAK/Fn14 pathway in health and disease", *Cytokine* 40:1-16 (2007).
Cardiel et al., "Abetimus Sodium for Renal Flare in Systemic Lupus Erythematosus", *Arthritis & Rheumatism* 58(8):2470-2480 (2008).
Dogra et al., "TNF-related weak inducer of apoptosis (TWEAK) is a potent skeletal muscle-wasting cytokine", *FASEB J.* 21:1857-1869 (2007).
Droz, D., "Clinico-anatomical forms of primary glomeruionephritis", *Rev. Med. Interne* 15(6):390-398 (1994) (Abstract only; article in French).
European Patent Application No. 11191771: Extended Search Report, including Search Opinion, dated Oct. 1, 2012.
European Patent Application No. 11191813: Extended Search Report, including Search Opinion, dated Oct. 1, 2012.
European Patent Application No. 12171177: Partial Search Report, dated Oct. 10, 2012.
European Patent Application No. 12171177: Extended Search Report, including Search Opinion, dated Mar. 1, 2013.
Girgenrath et al., "TWEAK, via its receptor Fn14, is a novel regulator of mesenchymal progenitor cells and skeletal muscle regeneration", *EMBO J.* 25:5826-5839 (2006).

(56) References Cited

OTHER PUBLICATIONS

*Harrison's Principles of Internal Medicine*, 2005; pp. 1960-1963.
International Search Report issued in International Patent Application No. PCT/US97/13945; Date of Mailing: Jan. 7, 1998.
Jones et al., "Immunospecific reduction of antioligonucleotide antibody-forming cells with a tetrakis-oligonucleotide conjugate (LJP 394), a therapeutic candidate for the treatment of lupus nephritis", *J. Med. Chem.* 38(12):2138-2144 (1995) (Abstract only).
Lantto et al., "Functional Consequences of Insertions and Deletions in the Complementarity-determining Regions of Human Antibodies", *J. Biol. Chem.* 277(47):45108-45114 (2002).
Markan et al., "Up regulation of the GRP-78 and GADD-153 and down regulation of Bcl-2 proteins in primary glomerular diseases: a possible involvement of the ER stress pathway in glomerulonephritis", *Mol. Cell Biochem.* 324:131-138 (2009).
Mittal et al., "The TWEAK-Fn14 system is a critical regulator of denervation-induced skeletal muscle atrophy in mice", *J. Cell Biol.* 188(6):833-849 (2009).
Morosetti et al., "TWEAK in Inclusion-Body Myositis Muscle—Possible Pathogenic Role of a Cytokine Inhibiting Myogenesis", *Am. J. Pathol.* 180(4):1603-1613 (2012).
Murphy, "Revisiting graft-versus-host disease models of autoimmunity: new insights in immune regulatory processes", *J. Clin. Invest.* 106(6):745-747 (2000).
Paul et al., "The E3 Ubiquitin Ligase TRAF6 Intercedes in Starvation-Induced Skeletal Muscle Atrophy through Multiple Mechanisms", *Mol. Cell. Biol.* 32(7):1248-1259 (2012).
Rus et al., "Kinetics of Th1 and Th2 Cytokine Production During the Early Course of Acute and Chronic Murine Graft-Versus-Host Disease", *J. immunol.* 155:2396-2406 (1995).
Tschetter et al., "Progression from Acute to Chronic Disease in a Murine Parent-into-$F_1$ Model of Graft-Versus-Host Disease", *J. Immunol.* 165:5987-5994 (2000).
Weisman et al., "Reduction in circulating dsDNA antibody titer after administration of LJP 394", *J. Rheumatol.* 24(2):314-318 (1997) (Abstract only).
Written Opinion issued in International Patent Application No. PCT/US97/13945: Date of Mailing: Jul. 27, 1998.

\* cited by examiner

FIG. 2: Effect of Combination Blocking of Tweak and TNF in mCIA (Day 38 metatarsal height measurement)

FIG. 4: TWEAK blocking mAbs are efficacious in both mouse and rat CIA models

FIG. 5: Effect of TWEAK Inhibition Occurs at or after the Challenge Phase

FIG. 7: Serum TWEAK levels during course of mCIA

METHODS FOR TREATING INFLAMMATORY BOWEL DISEASE

CROSS-REFERENCE TO RELATED APPLICATIONS

This application is a continuation of application Ser. No. 11/937,687, filed Nov. 9, 2007, abandoned, which is a continuation application claiming priority under 35 U.S.C. §120 of International Application No. PCT/US2006/018077, filed on May 10, 2006, and claims the benefit of U.S. Provisional Application No. 60/679,518, filed on May 10, 2005, all of which are incorporated herein by reference in their entirety.

BACKGROUND

The tumor-necrosis factor (TNF)-related cytokines are a superfamily of proteins that have an array of functions, including ones implicated in immune regulation and apoptosis regulation. Examples of TNF superfamily members include TNF-α and TWEAK (TNF-like weak inducer of apoptosis).

SUMMARY

As further described below, the TWEAK and TNF-α pathways work independently to mediate aspects of inflammation. Blocking both of the molecular signalling pathways modulated by TWEAK and TNF-α can be used to treat a variety of inflammatory disorders. Examples of such treatments are described below.

In one aspect, the disclosure features a method of treating a subject for an inflammatory disorder. In a preferred embodiment, the inflammatory disorder is an arthritic disorder, e.g., rheumatoid arthritis, psoriatic arthritis, or Sjögren's Syndrome. The method includes: administering, to a subject, e.g., a human subject, who has or is at risk for the disorder, e.g., rheumatoid arthritis, a TWEAK blocking agent in combination with a TNF-α blocking agent. The TWEAK blocking agent and the TNF-α blocking agent can be administered in amounts and for a time to provide a therapeutic effect, e.g., an overall therapeutic effect. The effect can be additive or, in some cases, synergistic. For example, the effect of both blocking agents may be a greater total effect than the sum of the individual effects, e.g., in a particular subject.

A variety of TWEAK blocking agents can be administered to a subject to block a interaction or activity of TWEAK or a TWEAK-R. A "TWEAK blocking agent" refers to an agent (e.g., any compound, e.g., an antibody or a soluble form of the TWEAK receptor) that at least partially inhibits an interaction or activity of a TWEAK or TWEAK-R. For example, the agent at least partially inhibits an activity, e.g., binding of TWEAK to a TWEAK-R, or the agent at least partially inhibits a nucleic acid encoding TWEAK or TWEAK-R, e.g., to reduce TWEAK or TWEAK-R protein expression.

In one embodiment, the agent reduces the ability of TWEAK to bind to a TWEAK receptor, e.g., Fn14. The agent can be a blocking antibody that binds to TWEAK or to Fn14. The antibody can be a full length IgG. In one embodiment, the antibody is human, humanized, or effectively human. In one embodiment, the TWEAK blocking antibody competes with AB.D3 (an antibody that has ATCC Accession No. HB-12622) for binding with TWEAK, is a humanized antibody AB.D3, comprises at least two, three, four, five, or six CDRs of AB.D3 (or CDRs that are at least overall 85, 90, 92, 95, 97% identical to such CDRs), and/or comprises antibody AB.D3 variable domains (or one or more variable domains that are at least overall 85, 90, 92, 95, 97% identical to such variable domains).

In one embodiment, the agent is a soluble form of a TWEAK receptor, e.g., a human TWEAK receptor such as Fn14. The soluble form of the TWEAK receptor can be fused to an antibody Fc region (e.g., a human Fc region). For example, the soluble form of the TWEAK receptor includes a sequence at least 95% identical to amino acids 28-$X_1$ of SEQ ID NO:2, where amino acid $X_1$ is selected from the group of residues 68 to 80 of SEQ ID NO:2.

A variety of TNF-α blocking agents can be administered to a subject to block an interaction or activity of TNF-α or a TNF-α receptor, e.g., TNFR-I, or TNFR-II. A "TNF-α blocking agent" refers to an agent (e.g., any compound, e.g., an antibody or a soluble form of a TNF-α receptor) that at least partially inhibits an interaction or activity of TNF-α or a TNF-α receptor. For example, the agent at least partially inhibits an activity, e.g., binding of TNF-α to a TNF-α receptor, or the agent at least partially inhibits a nucleic acid encoding TNF-α or a TNF-α receptor, e.g., to reduce TNF-α or TNF-α receptor protein expression.

In one embodiment, the TNF-α blocking agent reduces the ability of TNF-α to bind to a TNF-α, receptor. For example, the TNF-α blocking agent includes an antibody that binds to TNF-α, TNFR-I, or TNFR-II. Exemplary antibodies include infliximab or adalimumab. The TNF-α blocking agent can include a soluble form of a TNF-α receptor and optionally a Fc domain. For example, the TNF-α blocking agent is etanercept.

As used herein, "administered in combination" means that two or more agents (e.g., the TWEAK blocking agent and the TNF-α blocking agent) are administered to a subject at the same time or within an interval, such that there is overlap of an effect of each agent on the patient. Preferably the administrations of the first and second agent are spaced sufficiently close together such that a combinatorial effect is achieved. The interval can be an interval of hours, days or weeks. Generally, the agents are concurrently bioavailable, e.g., detectable, in the subject. In a preferred embodiment, at least one administration of one of the agents, e.g., the first agent (e.g., TNF-α blocking agent), is made while the other agent, e.g., the TWEAK blocking agent, is still present at a therapeutic level in the subject.

In one embodiment, the TWEAK blocking agent is administered between an earlier and a later administration of the TNF-α blocking agent. In other embodiments, the TNF-α blocking agent is administered between an earlier and a later administration of the TWEAK blocking agent. In a preferred embodiment, at least one administration of one of the agents, e.g., the TNF-α blocking agent, is made within 1, 7, 14, 30, or 60 days of the other agent, e.g., the TWEAK blocking agent.

In one embodiment, prior to administering the TWEAK blocking agent and TNF-α blocking agent, the subject was receiving either the TWEAK blocking agent or TNF-α blocking agent, but not the other. The subject may have had a response that did not meet a predetermined threshold, e.g., a stabilization or reduction in a total Sharp score or a Sharp erosion score. In another embodiment, the subject can be one who has not been previously administered the TNF-α blocking agent nor the TWEAK blocking agent for at least 3 months (e.g., at least 6 months, 9 months, or a year prior) prior to being administered the first and second agent in combination.

In one implementation, the TWEAK blocking agent and TNF-α blocking agent are provided as a co-formulation, and the co-formulation is administered to the subject. It is further possible, e.g., at least 24 hours before or after administering the co-formulation, to administer one of the agents separately from the other. In another implementation, the agents are provided as separate formulations, and the step of administering includes sequentially administering the agents. The sequential administrations can be provided on the same day (e.g., within one hour of one another or at least 3, 6, or 12 hours apart) or on different days.

Generally, the TWEAK blocking agent and TNF-α blocking agent are each administered as a plurality of doses separated in time, e.g., according to a regimen. The regimen for one or both may have a regular periodicity. The regimen for the TNF-α blocking agent can have a different periodicity from the regimen for the TWEAK blocking agent, e.g., one can be administered more frequently than the other. The agents can be administered by any appropriate method, e.g., subcutaneously, intramuscularly, or intravenously. The subject can be administered doses of the TNF-α blocking agent and doses of the TWEAK blocking agent for greater than 14 weeks, greater than six or nine months, greater than 1, 1.5, or 2 years.

In some embodiments, each of the agents is administered at about the same dose as the dose used for monotherapy. In other embodiments, the TNF-α blocking agent is administered at a dosage that is equal to or less than an amount required for efficacy if administered alone (e.g., at least 10, 20, 30, or 40% less). Likewise, the TWEAK blocking agent can be administered at a dosage that is equal to or less than an amount required for efficacy if administered alone (e.g., at least 10, 20, 30, or 40% less). For example, in some embodiments in which the subject has previously received the TNF-α blocking agent, the subject is administered a reduced dose of the TNF-α blocking agent after receiving the TWEAK blocking agent (relative to the dose of the TNF-α blocking agent received before receiving the TWEAK blocking agent for the first time). The same or a different TNF-α blocking agent can be used in the combination as was used in the previous monotherapy.

A subject can be evaluated after receiving the first and second agent, e.g., for indicia of responsiveness. A skilled artisan can use various clinical or other indicia of effectiveness of treatment. The subject can be monitored at various times during a regimen.

In one embodiment, the TWEAK blocking agent and the TNF-α blocking agent are administered in amounts effective to inhibit the collective effects of TWEAK and TNF-α pathways in cells that generate inflammatory signals, e.g., synoviocytes, chondrocytes, osteoclasts, osteoblasts, dermal fibroblasts, monocytes, macrophages, or endothelial cells. The agents can be administered in amounts effective to reduce transcription of a set of genes induced by TWEAK and TNF-α in such cells, e.g., to reduce transcription of genes synergistically activated by TWEAK and TNF-α, e.g., one or more genes list in Table 1 in synoviocytes, chondrocytes, osteoclasts, or osteoblasts.

In some embodiments, the TWEAK blocking agent is administered in an amount that is at least 20, 30, 50, 60, or 70% less than standard dosages for TWEAK blocking agent monotherapy (or a TWEAK blocking agent therapy in the absence of TNF-α, blocking agent) for treating an adult subject for rheumatoid arthritis. For example, the TWEAK blocking agent is administered in an amount less than that required to be effective as a monotherapy.

In some embodiments, the TNF-α blocking agent is administered in an amount that is at least 20, 30, 50, 60, or 70% less than standard dosages for a TNF-α blocking agent monotherapy (or a TNF-α, blocking agent therapy in the absence of a TWEAK blocking agent) for treating an adult subject for rheumatoid arthritis. For example, the TNF-α blocking agent is administered in an amount less than that required to be effective as a monotherapy. In other embodiments, the TNF-α blocking agent and the TWEAK blocking agent are administered in the same dose as that used in monotherapy.

For example, the subject is not receiving methotrexate. In one embodiment, the subject is not receiving any other disease modifying anti-rheumatic drug (DMARD), i.e., other than the TWEAK blocking agent and the TNF-α blocking agent.

The amounts can be sufficient to result in a statistically significant reduction in joint damage as measured by the Sharp erosion score. For example, the subject can be monitored at one or more instances for a parameter indicative of the disorder.

The method can include evaluating (e.g., monitoring one or times, e.g., periodically) the subject, e.g., for symptoms of the disorder or indicia that grade disorder severity. For example, in the case of rheumatoid arthritis, it is possible to use the total Sharp score (TSS), Sharp erosion score, HAQ disability index, or radiological method.

In another aspect, the disclosure features a method that includes: administering, to a subject (e.g., a human subject) who has or is at risk for rheumatoid arthritis, a TWEAK blocking agent in combination with another DMARD (e.g., a biologic DMARD), in amounts and for a time to provide an overall therapeutic effect. Some examples of DMARDs for treating rheumatoid arthritis are described herein.

In another aspect, the invention features a method of reducing joint inflammation in a subject in need thereof. The method includes administering to a subject who suffers from joint inflammation a TNF-α blocking agent in combination with a TWEAK blocking agent, e.g., as described herein. In some cases, the subject has an arthritic disorder, e.g., rheumatoid arthritis.

Also featured is a pharmaceutical composition that includes: a TWEAK blocking agent; and a DMARD, e.g., a TNF-α blocking agent or other DMARD.

Kits can also be provided that include a TWEAK blocking agent and a DMARD (e.g., a TNF-α blocking agent or other DMARD). The agents can be provided as separate pharmaceutical compositions or a single pharmaceutical composition. The kit can further include instructions for administration to treat rheumatoid arthritis, a device for administering the agents, and/or reagents for evaluating a parameter, e.g., a clinical parameter associated with the disorder.

In another aspect, the disclosure features a method that includes: identifying a subject who has inflammation mediated by TWEAK and TNF-α, and/or increased TWEAK expression or activity, and/or increased expression or activity of a biomarker whose expression is modulated (e.g., increased) by TWEAK (see, e.g., Table 2); and administering to the subject a therapy. For example, therapy can include administering: (i) a TWEAK blocking agent; (ii) a TNF-α blocking agent; or (iii) a combination of (i) and (ii). A "TWEAK/TNF-α synergistically activated cellular program" is a cellular state characterized by properties that result from stimulation by particular doses of both TWEAK and TNF-α, but which are not attained to a comparable degree by stimulation with that dose of TWEAK in the absence of that dose of TNF-α nor by stimulation by that dose TNF-α in the absence of that dose of TWEAK. The subject can be identified by evaluating expression of one or more genes in cells that generate inflammatory signals, e.g., synoviocytes, chondrocytes, osteoclasts, osteoblasts, or dermal fibroblasts, or associated tissue, obtained from the subject. The one or more genes from Table 1 can be evaluated. The subject can also be evaluated for one or more symptoms of rheumatoid arthritis.

In another aspect, the disclosure features a method that includes: administering, to a human subject who has or is at risk for rheumatoid arthritis, and who is being or has been withdrawn from a DMARD (other than a TWEAK blocking agent), a TWEAK blocking agent, e.g., in an amount and for a time effective to provide an overall therapeutic effect. The method can be used to treat a subject has not previously received a TWEAK blocking agent or who has not recently received a TWEAK blocking agent, e.g., within the last month, six months, or year.

In one embodiment, the DMARD that is being or has been withdrawn is a TNF-α blocking agent. The subject may have an inadequate response to the TNF-α blocking agent. As used herein, an "inadequate response" refers to a response that, as assessed by a patient or a skilled clinician, exhibits insufficient efficacy or intolerable or unacceptable toxicity. Insufficient efficacy can be defined by failure to meet a predetermined level of response to treatment. For example, the TNF-α blocking agent may cause toxicity, induce an immune-compromised state, or lacks efficacy, thereby prompting its withdrawal. For example, the subject is refractory to therapy with the TNF-α blocking agent. The subject may have, e.g., tuberculosis, an opportunistic infection, glomerulonephritis, a demyelinating syndrome, a lupus-like reaction, or a pathogenic bacterial infection. In some cases, an inadequate response is indicated by an adverse event detected during treatment with the TNF-α blocking agent.

The TNF-α blocking agent may have been administered within the previous year, three months, month, two weeks, or week. In some cases, the subject may still be administered the TNF-α blocking agent, but its dosage may be reduced or may be a final dosage, e.g., a dosage provided prior to complete termination. In other cases, administration of the TNF-α blocking agent is ceased such that, upon administration of one or more doses of the TWEAK blocking agent, the subject is no longer receiving the TNF-α blocking agent.

In other embodiments, the DMARD that is being or has been withdrawn is methotrexate, parenteral gold, sulphasalazine, or hydroxychloroquinone. For example, the DMARD is other than a TNF-α blocking agent. The DMARD can be withdrawn due to toxicity, immune suppression or lack of efficacy. For example, an adverse event may be detected during treatment with the DMARD.

In another aspect, the disclosure features a method that includes: detecting an adverse event in a human subject who has rheumatoid arthritis, and is being treated with a DMARD other than a TWEAK blocking agent; and administering, to the subject, a TWEAK blocking agent in an amount and for a time effective to provide an overall therapeutic effect.

In one embodiment, the subject is being treated with a TNF-α blocking agent. The method can further include withdrawing the TNF-α blocking agent. The adverse event can include a lupus-like reaction, a bacterial or opportunistic infection, or tuberculosis.

In one aspect, the disclosure features a method of treating a subject for an inflammatory disorder, particularly one that a TNF-α blocking agent does not exacerbate. The inflammatory disorder can be rheumatoid arthritis, or a disorder other than rheumatoid arthritis. For example, the disorder can be psoriatic arthritis, ankylosing spondylitis, inflammatory bowel disease (including ulcerative colitis and Crohn's disease), psoriasis, or inflammatory myositis. Still other examples of inflammatory disorders include Langerhans-cell histiocytosis, adult respiratory distress syndrome/bronchiolitis obliterans, Wegener's granulomatosis, vasculitis, cachexia, stomatitis, idiopathic pulmonary fibrosis, dermatomyositis or polymyositis, non-infectious scleritis, chronic sarcoidosis with pulmonary involvement, myelodysplastic syndromes/refractory anemia with excess blasts, ulcerative colitis, moderate to severe chronic obstructive pulmonary disease, and giant cell arteritis. The method includes administering, to a human subject who has or is at risk for an inflammatory disorder, a TWEAK blocking agent in an amount and for a time to provide an overall therapeutic effect. The method can include administering the TWEAK blocking agent in combination with a TNF-α blocking agent, in amounts and for a time to provide an overall therapeutic effect, or administering the TWEAK blocking agent without providing (e.g., withholding) the TNF-α blocking agent. In one embodiment, the subject is less than 17 years of age, and the disorder is juvenile rheumatoid arthritis or pediatric psoriasis. The method can include other features described herein.

In another aspect, the disclosure features a method of evaluating a test compound, e.g., for ability to modulate a TWEAK and/or TNF-α response in vitro or in vivo. A TWEAK response includes modulation of TWEAK itself or modulation of a TWEAK receptor. The method includes contacting the test compound to a cell, tissue, or organism, in the presence of TWEAK and/or TNF-α, e.g., exogenous TWEAK and/or TNF-α. The method further includes evaluating whether the test compound modulates ability of the cell, tissue, or organism to respond to TWEAK and/or TNF-α, e.g., to reduce TWEAK/TNF-α mediated cellular programs. The method can include evaluating expression or activity of one or more genes in Table 1 or Table 2. The method can further include evaluating ability of the test compound to modulate a disorder, e.g., using an animal model of a human disorder described herein.

In another aspect, the disclosure features a method of evaluating a subject, e.g., a human subject. The subject can be evaluated in advance of providing one or more agents described herein, while receiving one or more such agents, or after receiving one or more such agents. The method includes evaluating cells (e.g., in a sample obtained from the subject), tissue or other material from the subject to determine if expression (including protein and mRNA expression) of one or more genes in Table 2 are altered relative to a reference value. The reference value can be a value associated with a reference value for a normal subject, a control subject, or a value determined, e.g., for a cohort of subjects. The reference value can be a reference value for the subject him or herself, e.g., at another instance, e.g., before receiving one or more agents, and so forth. The information from the evaluating can be stored on a computer-readable medium or another medium, and/or communicated, e.g., using a computer network. The method can be used to determine if the patient is or is predicted to be TWEAK responsive. For example, a patient that has an elevated level of expression of one or more genes in Table 2 can be indicated to be TWEAK responsive. The method can include providing an indication that the subject is TWEAK responsive, and optionally instructions to administer a TWEAK blocking agent. The method can further include administering the TWEAK blocking agent.

In another aspect, the disclosure features a medicament comprising a TWEAK blocking agent and a TNF-α blocking agent, e.g., for use in therapy.

In another aspect, the disclosure features use of a TWEAK blocking agent and a TNF-α blocking agent for the preparation of a medicament, e.g., for the treatment of an inflammatory disorder described herein, e.g., joint inflammation or an arthritic disorder, e.g., rheumatoid arthritis.

In another aspect, the disclosure features use of a TWEAK blocking agent for the preparation of a medicament, e.g., for the treatment of an inflammatory disorder described herein, e.g., joint inflammation or an arthritic disorder, e.g., rheumatoid arthritis in subjects who are unresponsive to therapy with another DMARD.

All patents, patent applications, and references cited herein are hereby incorporated by reference in their entireties. In the case of conflict, the present application controls.

The term "synergy" refers to a result from at least two events that is greater than the sum of the result of each event individually. ANOVAs can be used to determine a synergy factor in the following equation:

$$R = A + B + \epsilon(A*B)$$

Exemplary values for the synergy factor $\epsilon$ can be greater than zero or a predetermined value, e.g., 1, 2, or more.

The term "treating" refers to administering a therapy in an amount, manner, and/or mode effective to improve or prevent a condition, symptom, or parameter associated with a disorder or to prevent onset, progression, or exacerbation of the disorder, to either a statistically significant degree or to a degree detectable to one skilled in the art. Accordingly, treating can achieve therapeutic and/or prophylactic benefits. An effective amount, manner, or mode can vary depending on the subject and may be tailored to the subject.

Reference to inhibition includes at least partial inhibition as well as other degrees of inhibition, e.g., substantial or complete.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
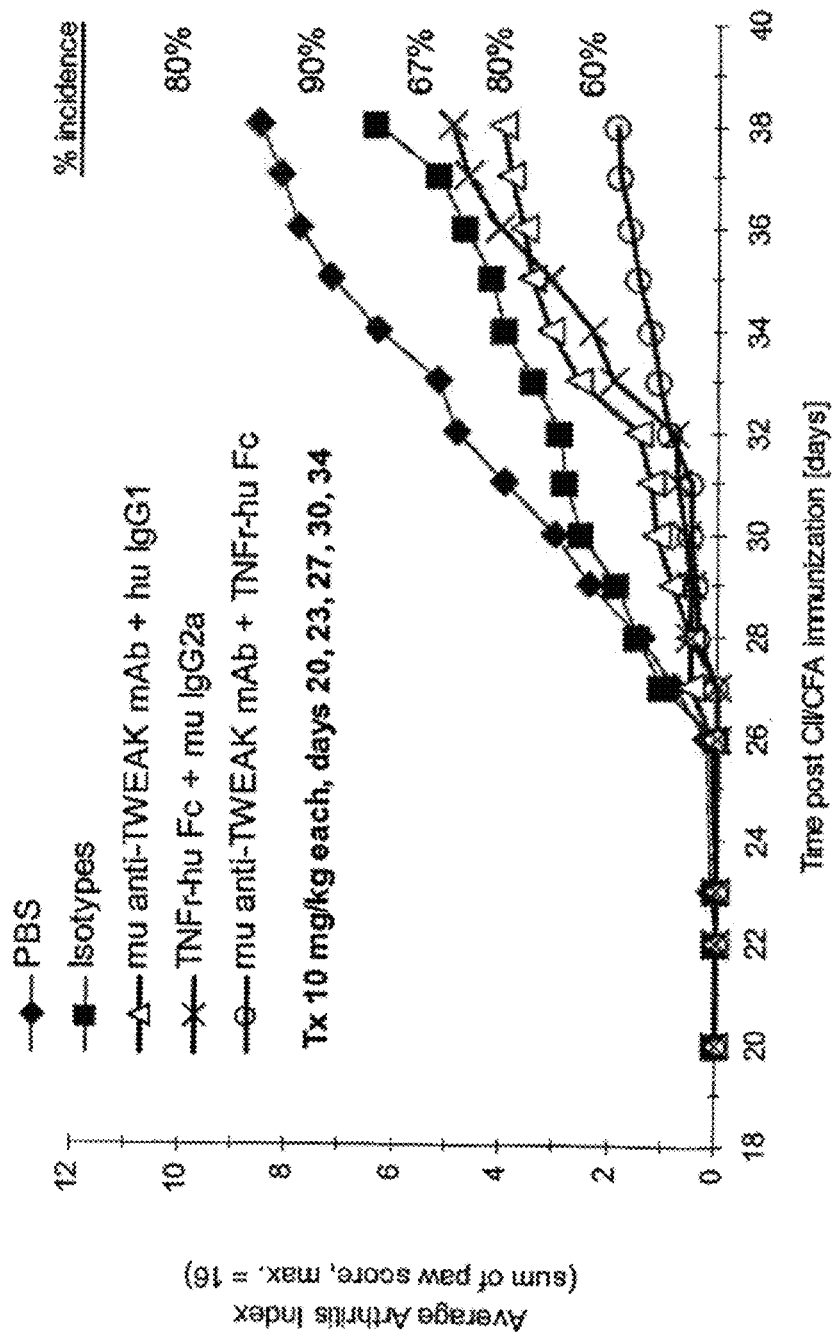
FIG. 1 is a line graph showing average arthritis index scores in a mCIA model of arthritis in mice that were treated with a combination of TWEAK and TNF-α blocking agents, a TWEAK blocking agent alone, a TNF-α blocking agent alone, a PBS control, or isotype-matched controls.

We have discovered that the TWEAK and TNF-α pathways independently contribute to inflammatory responses, e.g., in synovial cells present in joints, and that both TWEAK and TNF-α can independently activate similar sets of genes indicating redundancy between the two pathways. Accordingly, reducing the activity of both pathways provides an advantageous therapeutic route to ameliorating inflammation, e.g., in joints, e.g., in arthritic conditions. Concurrent blocking of both TWEAK and TNF-α pathways proved beneficial in a mouse model of rheumatoid arthritis (mCIA) and achieved results greater than blocking one of these pathways.

In addition to rheumatoid arthritis, reducing activity of both pathways may be used to treat in other disorders, e.g., other inflammatory disorders such as psoriatic arthritis, ankylosing spondylitis, inflammatory bowel disease, psoriasis, inflammatory myositis, and other disorders disclosed herein. A variety of methods can be used to reduce activity of the TWEAK and TNF-α pathways. For example, it is possible to administer a TWEAK blocking agent in combination with a TNF-α blocking agent. Examples of these and other agents are further described below.

In some implementations, therapeutic benefit can be achieved by reducing one of the two pathways. For example, a TWEAK blocking agent can be administered to a subject who has an inadequate response to a therapeutic that modulates just one of the pathways, e.g., an inadequate response to a TNF-α blocking agent or an inadequate response to a TWEAK blocking agent. A TWEAK blocking agent can also be administered to a subject who is or who is planning to withdraw from a DMARD treatment with another agent, e.g., an agent other than a TNF-α blocking agent.

TWEAK Blocking Agents

A variety of agents can be used as a TWEAK blocking agent. The agent may be any type of compound (e.g., small organic or inorganic molecule, nucleic acid, protein, or peptide mimetic) that can be administered to a subject. In one embodiment, the blocking agent is a biologic, e.g., a protein having a molecular weight of between 5-300 kDa. For example, a TWEAK blocking agent may inhibit binding of TWEAK to a TWEAK receptor or may prevent TWEAK-mediated NF-κB activation. A typical TWEAK blocking agent can bind to TWEAK or a TWEAK receptor, e.g., Fn14. A TWEAK blocking agent that binds to TWEAK or a TWEAK receptor may alter the conformation of TWEAK or a TWEAK receptor, block the binding site on TWEAK or a TWEAK receptor, or otherwise decrease the affinity of TWEAK for a TWEAK receptor or prevent the interaction between TWEAK and a TWEAK receptor.

A TWEAK blocking agent (e.g., an antibody) may bind to TWEAK or to a TWEAK receptor with a $K_d$ of less than $10^{-6}$, $10^{-7}$, $10^{-8}$, $10^{-9}$, or $10^{-10}$ M. In one embodiment, the blocking agent binds to TWEAK with an affinity at least 5, 10, 20, 50, 100, 200, 500, or 1000-fold better than its affinity for TNF-α or another TNF superfamily member (other than TWEAK). In one embodiment, the blocking agent binds to the TWEAK receptor with an affinity at least 5, 10, 20, 50, 100, 200, 500, or 1000-fold better than its affinity for the TNF receptor or a receptor for another TNF superfamily member. A preferred TWEAK blocking agent specifically binds TWEAK or TWEAK-R.

Exemplary TWEAK protein molecules include human TWEAK (e.g., AAC51923, shown as SEQ ID NO:1)), mouse TWEAK (e.g., NP_035744.1), rat TWEAK (e.g., XP_340827.1), and *Pan troglodytes* TWEAK (e.g., XP_511964.1). Also included are proteins that include an amino acid sequence at least 90, 92, 95, 97, 98, 99% identical or completely identical to the mature processed region of the aforementioned TWEAK proteins (e.g., an amino acid sequence at least 90, 92, 95, 97, 98, 99% identical or completely identical to amino acids $X_1$-249 of SEQ ID NO:1, where amino acid $X_1$ is selected from the group of residues 75-115 of SEQ ID NO:1, e.g., $X_1$ is residue Arg 93 of SEQ ID NO:1) and proteins encoded by a nucleic acid that hybridizes under high stringency conditions to a human, mouse, rat, or *Pan troglodytes* gene encoding a naturally occurring TWEAK protein. Preferably, a TWEAK protein, in its processed mature form, is capable of providing at least one TWEAK activity, e.g., ability to activate Fn14.

Exemplary Fn14 protein molecules include human Fn14 (e.g., NP_057723.1, shown as SEQ ID NO:2), mouse Fn14 (e.g., NP_038777.1), and rat Fn14 (e.g., NP 851600.1) as well as soluble proteins that include an amino acid sequence at least 90, 92, 95, 97, 98, 99% identical or completely identical to the extracellular domain of Fn14 (and TWEAK-binding fragments thereof) and proteins encoded by a nucleic acid that hybridizes under high stringency conditions to a human, mouse, rat, or *Pan troglodytes* gene encoding a naturally occurring Fn14 protein. Preferably, a Fn14 protein useful in the methods described herein is a soluble Fn14 (lacking a transmembrane domain) that includes a region that binds to a TWEAK protein, e.g., an amino acid sequence at least 90, 92, 95, 97, 98, or 99% identical, or completely identical, to amino acids 28-$X_1$ of SEQ ID NO:2, where amino acid $X_1$ is selected from the group of residues 68 to 80 of SEQ ID NO:2.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences. Alignments of related proteins described herein are instructive for identifying amino acid positions that tolerate modification, e.g., insertion, deletion, and substitution, e.g., conservative or non-conservative substitution.

As used herein, the term "hybridizes under high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Exemplary TWEAK blocking agents include antibodies that bind to TWEAK or TWEAK-R and soluble forms of the TWEAK-R that compete with cell surface TWEAK-R for binding to TWEAK. An example of a soluble form of the TWEAK-R is an Fc fusion protein that includes at least a portion of the extracellular domain of TWEAK-R (e.g., a soluble TWEAK-binding fragment of TWEAK-R), referred to as TWEAK-R-Fc. Other soluble forms of TWEAK-R, e.g., forms that do not include an Fc domain, can also be used. Antibody blocking agents are further discussed below.

Other types of blocking agents, e.g., small molecules, nucleic acid or nucleic acid-based aptamers, and peptides, can be isolated by screening, e.g., as described in Jhaveri et al. *Nat. Biotechnol.* 18:1293 and U.S. Pat. No. 5,223,409. Exemplary assays for determining if an agent binds to TWEAK or TWEAK-R and for determining if an agent modulates a TWEAK/TWEAK-R interaction are described, e.g., in U.S. 2004-0033225.

An exemplary soluble form of the TWEAK-R protein includes a region of the TWEAK-R protein that binds to TWEAK, e.g., about amino acids 32-75, 31-75, 31-78, or 28-79 of SEQ ID NO:2. This region can be physically associated, e.g., fused to another amino acid sequence, e.g., an Fc domain, at its N- or C-terminus. The region from TWEAK-R can be spaced by a linker from the heterologous amino acid sequence. U.S. Pat. No. 6,824,773 describes an exemplary TWEAK-R fusion protein.

TNF-α Blocking Agents

A variety of agents can be used as a TNF-α blocking agent. The agent may be any type of compound (e.g., small organic or inorganic molecule, nucleic acid, protein, or peptide mimetic) that can be administered to a subject. In one embodiment, the blocking agent is a biologic, e.g., a protein having a molecular weight of between 5-300 kDa. For example, a TNF-α blocking agent may inhibit binding of TNF-α to a TNF-α receptor or otherwise prevent TNF-α receptor downstream signalling. A typical TNF-α blocking agent can bind to TNF-α or a TNF-α receptor, e.g., TNFR-I or TNFR-II. A TNF-α blocking agent that binds to TNF-α or a TNF-α receptor may alter the conformation of TNF-α or a TNF-α receptor, block the binding site on TNF-α or a TNF-α receptor, or otherwise decrease the affinity of TNF-α for a TNF-α receptor or prevent the interaction between TNF-α and a TNF-α receptor.

A TNF-α blocking agent (e.g., an antibody) may bind to TNF-α or to a TNF-α receptor with a $K_d$ of less than $10^{-6}$, $10^{-7}$, $10^{-8}$, $10^{-9}$, or $10^{-10}$ M. In one embodiment, the blocking agent binds to TNF-α with an affinity at least 5, 10, 20, 50, 100, 200, 500, or 1000-fold better than its affinity for TWEAK or another TNF superfamily member (other than TNF-α). A preferred TNF-α blocking agent specifically binds TNF-α or a TNF-α-R, such as a TNF-α or TNF-α-R specific antibody.

Exemplary TNF-α blocking agents include antibodies that bind to TNF-α or TNF-α-R and soluble forms of the TNF-α-R that compete with cell surface TNF-α-R for binding to TNF-α. An example of a soluble form of the TNF-α-R is an Fc fusion protein that includes at least a portion of the extracellular domain of TNF-α-R (e.g., a soluble TNF-α-binding fragment of TNF-α-R), referred to as TNF-α-R-Fc. Other soluble forms of TNF-α-R, e.g., forms that do not include an Fc domain, can also be used. Antibody blocking agents are further discussed below.

An exemplary soluble form of a TNF-α receptor protein is ENBREL®. See e.g., Arthritis & Rheumatism (1994) Vol. 37, 5295; J. Invest. Med. (1996) Vol. 44, 235A. U.S. Pat. No. 6,572,852 describes additional examples. The recommended dose of ENBREL® for adult patients with rheumatoid arthritis, psoriatic arthritis, or ankylosing spondylitis is 50 mg per week given as one subcutaneous (SC) injection using a 50 mg/mL single-use prefilled syringe. In addition to ENBREL®, other similar and/or corresponding regions of TNF-α receptors can be physically associated, e.g., fused to another amino acid sequence, e.g., an Fc domain, at its N- or C-terminus.

Other well characterized examples of TNF-α blocking agents include: infliximab (REMICADE®), a chimeric antibody that binds to tumor necrosis factor-alpha (TNF-α) and adalimumab (HUMIRA®), a human antibody that binds to TNF-α. For example, the recommended dose of REMICADE® is 3 mg/kg given as an intravenous infusion followed with additional similar doses at 2 and 6 weeks after the first infusion then every 8 weeks thereafter.

Additional examples of TNF-α blocking agents include chimeric, humanized, human or in vitro generated antibodies (or antigen-binding fragments thereof) to TNF (e.g., human TNF-α), such as D2E7, (human TNF-α antibody, U.S. Pat. No. 6,258,562; BASF), CDP-571/CDP-870/BAY-10-3356 (humanized anti-TNF-α antibody; Celltech/F' harmacia), cA2 (chimeric anti-TNFα antibody; REMICADE™, Centocor, also mentioned above); anti-TNF antibody fragments (e.g., CPD870); soluble fragments of the TNF receptors, e.g., p55 or p75 human TNF receptors or derivatives thereof, e.g., 75 kd TNFR-IgG (75 kD TNF receptor-IgG fusion protein, ENBREL™), p55 kd TNFR-IgG (55 kD TNF receptor-IgG fusion protein (LENERCEPT™)); enzyme antagonists, e.g., TNFα converting enzyme (TACE) inhibitors (e.g., an alpha-sulfonyl hydroxamic acid derivative, PCT Application WO 01/55112, and N-hydroxyformamide TACE inhibitor GW 3333, -005, or -022); and TNF-bp/s-TNFR (soluble TNF binding protein; see e.g., Arthritis & Rheumatism (1996) Vol. 39, No. 9 (supplement), S284; Amer. J. Physiol.—Heart and Circulatory Physiology (1995) Vol. 268, pp. 37-42).

Antibodies

Exemplary TWEAK blocking agents include antibodies that bind to TWEAK and/or TWEAK-R. In one embodiment, the antibody inhibits the interaction between TWEAK and a TWEAK receptor, e.g., by physically blocking the interaction, decreasing the affinity of TWEAK and/or TWEAK-R for its counterpart, disrupting or destabilizing TWEAK complexes, sequestering TWEAK or a TWEAK-R, or targeting TWEAK or TWEAK-R for degradation. In one embodiment, the antibody can bind to TWEAK or TWEAK-R at one or more amino acid residues that participate in the binding interface between TWEAK and its receptor. Such amino acid residues can be identified, e.g., by alanine scanning. In another embodiment, the antibody can bind to residues that do not participate in the binding interface. For example, the antibody can alter a conformation of TWEAK or TWEAK-R and thereby reduce binding affinity, or the antibody may sterically hinder binding. In one embodiment, the antibody can prevent activation of a TWEAK-R mediated event or activity (e.g., NF-κB activation).

Similarly, exemplary TNF-α blocking agents include antibodies that bind to TNF-α and/or a TNF-α receptor, e.g., TNFR-I or TNFR-II. In one embodiment, the antibody inhibits the interaction between TNF-α and a TNF-α receptor, e.g., by physically blocking the interaction, decreasing the affinity of TNF-α and/or TNF-α-R for its counterpart, disrupting or destabilizing TNF-α complexes, sequestering TNF-α or a TNF-α receptor, or targeting TNF-α or TNF-α receptor for degradation. In one embodiment, the antibody can bind to TNF-α or TNF-α receptor at one or more amino acid residues that participate in the TNF-α/TNF-α receptor binding interface. Such amino acid residues can be identified, e.g., by alanine scanning. In another embodiment, the antibody can bind to residues that do not participate in the TNF-α/TNF-α receptor binding. For example, the antibody can alter a conformation of TNF-α or TNF-α receptor and thereby reduce binding affinity, or the antibody may sterically hinder TNF-α/TNF-α receptor binding.

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$ fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A., et al. (1991) *Sequences of Proteins of Immunological Interest*, Fifth Edition, U.S. Department of Health and Human Services, NIH Publication No. 91-3242; and Chothia, C. et al. (1987) *J. Mol. Biol*. 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay (1988) *Ann. Rev Immunol*. 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two, or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with a target protein, e.g., TWEAK, a TWEAK receptor, TNF-α, TNFR-I, or TNFR-II.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Antibody Generation

Antibodies that bind to a target protein (e.g., TWEAK, TWEAK-R, TNF-α, TNFR-I or TNFR-II) can be generated by a variety of means, including immunization, e.g., using an animal, or in vitro methods such as phage display. All or part of the target protein can be used as an immunogen or as a target for selection. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nat. Gen.* 7:13-21; U.S. 2003-0070185; U.S. Pat. No. 5,789,650; and PCT Application WO 96/34096.

Non-human antibodies to the target proteins can also be produced, e.g., in a rodent. The non-human antibody can be humanized, e.g., as described in EP 239 400; U.S. Pat. Nos. 6,602,503; 5,693,761; and 6,407,213, deimmunized, or otherwise modified to make it effectively human.

EP 239 400 (Winter et al.) describes altering antibodies by substitution (within a given variable region) of their complementarity determining regions (CDRs) for one species with those from another. Typically, CDRs of a non-human (e.g., murine) antibody are substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody.

Other methods for humanizing antibodies can also be used. For example, other methods can account for the three dimensional structure of the antibody, framework positions that are in three dimensional proximity to binding determinants, and immunogenic peptide sequences. See, e.g., PCT Application WO 90/07861; U.S. Pat. Nos. 5,693,762; 5,693,761; 5,585,089; and 5,530,101; Tempest et al. (1991) *Biotechnology* 9:266-271 and U.S. Pat. No. 6,407,213. Still another method is termed "humaneering" and is described, for example, in U.S. 2005-008625.

Fully human monoclonal antibodies that bind to target proteins can be produced, e.g., using in vitro-primed human splenocytes, as described by Boerner et al. (1991) *J. Immunol.* 147:86-95. They may be prepared by repertoire cloning as described by Persson et al. (1991) *Proc. Nat. Acad. Sci. USA* 88:2432-2436 or by Huang and Stollar (1991) *J. Immunol. Methods* 141:227-236; also U.S. Pat. No. 5,798,230. Large non-immunized human phage display libraries may also be used to isolate high affinity antibodies that can be developed as human therapeutics using standard phage technology (see, e.g., Hoogenboom et al. (1998) *Immunotechnology* 4:1-20; Hoogenboom et al. (2000) *Immunol Today* 2:371-378; and U.S. 2003-0232333).

Antibody and Protein Production

Antibodies and other proteins described herein can be produced in prokaryotic and eukaryotic cells. In one embodiment, the antibodies (e.g., scFv's) are expressed in a yeast cell such as *Pichia* (see, e.g., Powers et al. (2001) *J. Immunol. Methods* 251:123-35), *Hanseula*, or *Saccharomyces*.

Antibodies, particularly full length antibodies, e.g., IgG's, can be produced in mammalian cells. Exemplary mammalian host cells for recombinant expression include Chinese Hamster Ovary (CHO cells) (including dhfr-CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr⁻ host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies (and Fc fusions) may also include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some proteins that include an Fc domain, the antibody/protein production system may be designed to synthesize antibodies or other proteins in which the Fc region is glycosylated. For example, the Fc domain of IgG molecules is glycosylated at asparagine 297 in the CH2 domain. The Fc domain can also include other eukaryotic post-translational modifications. In other cases, the protein is produced in a form that is not glycosylated.

Antibodies and other proteins can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody or Fc fusion protein. The protein can be purified from the milk, or for some applications, used directly.

Methods described in the context of antibodies can be adapted to other proteins, e.g., Fc fusions and soluble receptor fragments.

Nucleic Acid Blocking Agents

In certain implementations, nucleic acid blocking agents are used to decrease expression of a target protein such as TWEAK, a TWEAK-R (e.g., Fn14), TNF-α, TNFR-I or TNFR-II. These agents can be used in place of or in addition to proteinaceous TWEAK blocking agents and TNF-α blocking agents. In one embodiment, the nucleic acid antagonist is an siRNA that is directed against the mRNA produced from an endogenous gene that encodes the target protein. For example, the siRNA includes a region complementary to the mRNA. Other types of antagonistic nucleic acids can also be used, e.g., a dsRNA, a ribozyme, a triple-helix former, or an antisense nucleic acid.

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-9947, U.S. Pub. Apps. 2003-0166282; 2003-0143204; 2004-0038278; and 2003-0224432.

Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding a target protein) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding a target protein. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynyl-cytosine and C5-propynyluracil, to mention but a few. Descriptions of a variety of nucleic acid agents are available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

The nucleic acids described herein, e.g., an anti-sense nucleic acid described herein, can be incorporated into a gene construct to be used as a part of a gene therapy protocol to deliver nucleic acids that can be used to express and produce agents, e.g., anti-sense nucleic acids within cells. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. Protocols for producing recombinant retroviruses and for infecting cells in vitro or in to vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. Nos. 4,868,116 and 4,980,286; PCT Applications WO 89/07136; WO 89/02468; WO 89/05345; and WO 92/07573).

Another viral gene delivery system utilizes adenovirus-derived vectors. See, for example, Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are known to those skilled in the art.

Yet another viral vector system useful for delivery of the subject gene is the adeno-associated virus (AAV). See, for example, Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973).

Artificial Transcription Factors

Artificial transcription factors can also be used to regulate expression of a target protein, e.g., TWEAK, a TWEAK-R (e.g., Fn14), TNF-α, TNFR-I or TNFR-II. The artificial transcription factor can be designed or selected from a library, e.g., for ability to bind to a sequence in an endogenous gene encoding target protein, e.g., in a regulatory region, e.g., the promoter. For example, the artificial transcription factor can be prepared by selection in vitro (e.g., using phage display, U.S. Pat. No. 6,534,261) or in vivo, or by design based on a recognition code (see, e.g., PCT Application WO 00/42219 and U.S. Pat. No. 6,511,808). See, e.g., Rebar et al. (1996) *Methods Enzymol* 267:129; Greisman and Pabo (1997) *Science* 275:657; Isalan et al. (2001) *Nat. Biotechnol* 19:656; and Wu et al. (1995) *Proc. Natl. Acad. Sci. USA* 92:344 for, among other things, methods for creating libraries of varied zinc finger domains.

Optionally, an artificial transcription factor can be fused to a transcriptional regulatory domain, e.g., an activation domain to activate transcription or a repression domain to repress transcription. In particular, repression domains can be used to decrease expression of endogenous genes encoding TWEAK or TWEAK-R. The artificial transcription factor can itself be encoded by a heterologous nucleic acid that is delivered to a cell or the protein itself can be delivered to a cell (see, e.g., U.S. Pat. No. 6,534,261). The heterologous nucleic acid that includes a sequence encoding the artificial transcription factor can be operably linked to an inducible promoter, e.g., to enable fine control of the level of the artificial transcription factor in the cell.

Rheumatoid Arthritis (RA)

Rheumatoid arthritis ("RA") is a chronic inflammatory disease that causes pain, swelling, stiffness, and loss of function, primarily in joints. RA frequently begins in the synovium, the membrane that surrounds a joint creating a protective sac. In many individuals suffering from RA, leukocytes infiltrate from the circulation into the synovium causing continuous abnormal inflammation (e.g., synovitis). Consequently, the synovium becomes inflamed, causing warmth, redness, swelling, and pain. The collagen in the cartilage is gradually destroyed, narrowing the joint space and eventually damaging bone. The inflammation causes erosive bone damage in the affected area. During this process, the cells of the synovium grow and divide abnormally, making the normally thin synovium thick and resulting in a joint that is swollen and puffy to the touch.

As RA progresses, abnormal synovial cells can invade and destroy the cartilage and bone within the joint. The surrounding muscles, ligaments, and tendons that support and stabilize the joint can become weak and unable to work normally. RA also may cause more generalized bone loss that may lead to osteoporosis, making bones fragile and more prone to fracture. All of these effects cause the pain, impairment and deformities associated with RA. Regions that can be effected include the wrists, knuckles, knees and the ball of the foot. Often, many joints may be involved, and even the spine can be affected. In about 25% of people with RA, inflammation of small blood vessels can cause rheumatoid nodules, or lumps, under the skin. These are bumps under the skin that often form close to the joints. As the disease progresses, fluid may also accumulate, particularly in the ankles. Many patients with RA also develop anemia, or a decrease in the normal number of red blood cells.

RA encompasses a number of disease subtypes, such as Felty's syndrome, seronegative RA, "classical" RA, progressive and/or relapsing RA, and RA with vasculitis. Some experts classify the disease into type 1 or type 2. Type 1, the less common form, lasts a few months at most and leaves no permanent disability. Type 2 is chronic and lasts for years, sometimes for life. RA can also manifest as subcutaneous rheumatoid nodules, visceral nodules, vasculitis causing leg ulcers or mononeuritis multiplex, pleural or pericardial effusions, lymphadenopathy, Felty's syndrome, Sjogren's syndrome, and episcleritis. These disease subtypes and also subjects showing one or more of the above symptoms can be treated using the methods described herein.

RA occurs across all races and ethnic groups. At least one genetic predisposition has been identified and, in white populations, localized to a pentapeptide in the HLA-DR 1 locus of class II histocompatibility genes.

RA can be assessed by a variety of clinical measures. Some exemplary indicia include the total Sharp score (TSS), Sharp erosion score, and the HAQ disability index. The methods herein can be used to achieve an improvement for at least one of these indicia.

Non-Responders to TNF-α Blocking agents

In one aspect, subjects who have rheumatoid arthritis, or who are at risk for RA, or who have or at risk for another disorder described herein, can be evaluated for a parameter predictive of their ability to respond to a particular agent (e.g., a biologic DMARD), e.g., their ability to respond to a TNF-α blocking agent such as etanercept, infliximab, or adalimumab. For example, the parameter can be the presence or absence of a nucleotide in a gene encoding TNF-α. Subjects who are indicated to be less or non-responsive to a particular agent can be administered an alternative agent. For example, subjects who are indicated as non-responsive to etanercept can be administered a TWEAK blocking agent.

Rheumatoid arthritis patients with the T allele of TNFA-857C/T SNP may respond better to etanercept therapy than homozygotes for the C allele. Kang et al. *Rheumatology* 2005 April; 44(4):547-52. Accordingly, RA patients that are homozygous for the C allele can be treated with a TWEAK blocking agent, and etanercept or other TNF-α blocking agent can be withheld, or dosages can be reduced, e.g., relative to a standard dose.

Non-Responders to RA Therapies

A variety of treatments for RA, in addition to TNF-α blocking agents, are available. Many of these are therapeutics classified as disease modifying anti-rheumatic drugs (DMARDs). Traditional DMARDS include PLAQUENIL® (hydroxychloroquine), AZULFIDINE® (sulfasalazine) or RHEUMATREX® (methotrexate). For rheumatoid arthritis, it has been observed that the withdrawal rate from DMARD treatment in rheumatoid arthritis increases with the length of time the patient has been receiving the drug and that a number of these withdrawals relate to loss of efficacy (see, e.g., *Annals of the Rheumatic Diseases* (2003) 62:95-96). Accordingly, a TWEAK blocking agent can also be administered to a subject who has an inadequate response to a DMARD treatment, e.g., an inadequate response to treatment with one of the following agents:

a. Nonsteroidal anti-inflammatory drugs including salicylates, such as aspirin.

b. Gold compounds. In some patients, gold may produce clinical remission and decrease the formation of new bony erosions. Parenteral preparations include gold sodium thiomalate or gold thioglucose. Gold should be discontinued when signs of toxicity appear. Minor toxic manifestations (e.g., mild pruritus, minor rash) may be eliminated by temporarily withholding gold therapy, then resuming it cautiously about 2 weeks after symptoms have subsided. However, if toxic symptoms progress, gold should be withheld. A TWEAK blocking agent can be administered when gold is being discontinued or when a gold chelating drug (such as dimercaprol) is being administered to counteract gold toxicity.

c. Hydroxychloroquine can also control symptoms of mild or moderately active RA. Toxic effects usually are mild and include dermatitis, myopathy, and generally reversible corneal opacity. However, irreversible retinal degeneration has been reported. Hydroxychloroquine can be withdrawn and replaced, e.g., with a TWEAK blocking agent, e.g., upon detection of one or more of these side effects.

d. Oral penicillamine may have a benefit similar to gold. Side effects requiring discontinuation are more common than with gold and include marrow suppression, proteinuria, nephrosis, other serious toxic effects (e.g., myasthenia gravis, pemphigus, Goodpasture's syndrome, polymyositis, a lupus-like syndrome), rash, and a foul taste. Oral penicillamine can be withdrawn and replaced, e.g., with a TWEAK blocking agent, e.g., upon detection of one or more of these side effects.

e. Steroids are highly effective short-term anti-inflammatory drugs. However, their clinical benefit for RA often diminishes with time. Steroids do not predictably prevent the progression of joint destruction. Furthermore, severe rebound often follows the withdrawal of corticosteroids in active disease. Accordingly, a TWEAK blocking agent can be administered, prior to withdrawal, during withdrawal, or subsequent to complete withdrawal. Other side effect which can trigger withdrawal and use of a TWEAK blocking agent include peptic ulcer, hypertension, untreated infections, diabetes mellitus, and glaucoma.

f. Immunosuppressive drugs can be used in management of severe, active RA. However, major side effects can occur, including liver disease, pneumonitis, bone marrow suppression, and, after long-term use of azathioprine, malignancy. Withdrawal from immunosuppressive drugs can include administering a TWEAK blocking agent, e.g., upon detection of a side effect.

Alternatively, a TWEAK blocking agent can be administered to a subject who is receiving another treatment for RA, e.g., one of the above treatments. The combination of the treatment and the TWEAK blocking agent can be used to achieve additional therapeutic benefit and, optionally, to reduce the dosage of the other treatment. As result, side effects and other issues can be mitigated.

The methods described herein, e.g., a TWEAK blocking agent monotherapy or a combination therapy (such as with TWEAK and TNF-α blocking agents), can be used to treat a subject who has one or more severe complications of RA. Such complications include joint destruction, gastrointestinal bleeding, heart failure, pericarditis, pleuritis, lung disease, anemia, low or high platelets, eye disease, cervical (neck) spine instability, neuropathy, and vasculitis.

Other Disorders

The methods described herein can also be used to treat other inflammatory, immune, or autoimmune disorders in patients, for example disorders that are not exacerbated by administration of a TNF-α blocking agent. Examples of disorders that can be treated include psoriatic arthritis, ankylosing spondylitis, inflammatory bowel disease (including ulcerative colitis and Crohn's disease), psoriasis, or inflammatory myositis. Still other examples of inflammatory disorders include Langerhans-cell histiocytosis, adult respiratory distress syndrome/bronchiolitis obliterans, Wegener's granulomatosis, vasculitis, cachexia, stomatitis, idiopathic pulmonary fibrosis, dermatomyositis or polymyositis, non-infectious scleritis, chronic sarcoidosis with pulmonary involvement, myelodysplastic syndromes/refractory anemia with excess blasts, ulcerative colitis, moderate to severe chronic obstructive pulmonary disease, and giant cell arteritis.

A subject who is at risk for, diagnosed with, or who has one of these disorders can be administered a TWEAK blocking agent in an amount and for a time to provide an overall therapeutic effect. The TWEAK blocking agent can be administered in combination with a TNF-α blocking agent or without providing (e.g., withholding) the TNF-α blocking agent. In the case of a combination therapy, the amounts and times of administration can be those that provide, e.g., an enhanced or synergistic therapeutic effect. Further, the administration of the TWEAK blocking agent (with or without the TNF-α blocking agent) can be used as a primary, e.g., first line treatment, or as a secondary treatment, e.g., for subjects who have an inadequate response to a previously administered therapy (i.e., a therapy other than one with a TWEAK block agent).

Pharmaceutical Compositions

A TWEAK blocking agent (e.g., an antibody or soluble TWEAK-R protein, e.g., TWEAK-R-Fc) can be formulated as a pharmaceutical composition, e.g., for administration to a subject to treat a disorder described herein, e.g., an inflammatory disorder such as rheumatoid arthritis or other disorder described herein. A TNF-α blocking agent can be similarly formulated, either in the same composition or as a separate composition.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) *J. Pharm. Sci.* 66:1-19).

Pharmaceutical formulation is a well-established art, and is further described, e.g., in Gennaro (ed.), *Remington: The Science and Practice of Pharmacy*, 20$^{th}$ ed., Lippincott, Williams & Wilkins (2000) (ISBN: 0683306472); Ansel et al., *Pharmaceutical Dosage Forms and Drug Delivery Systems*, 7$^{th}$ Ed., Lippincott Williams & Wilkins Publishers (1999) (ISBN: 0683305727); and Kibbe (ed.), *Handbook of Pharmaceutical Excipients* American Pharmaceutical Association, 3$^{rd}$ ed. (2000) (ISBN: 091733096X).

In one embodiment, the TWEAK blocking agent (e.g., an antibody or TWEAK-R-Fc) and/or the TNF-α blocking agent is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and infrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the TWEAK blocking agent and/or the TNF-α blocking agent may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

A TWEAK blocking agent (e.g., an antibody or soluble TWEAK-R protein) can be modified, e.g., with a moiety that improves its stabilization and/or retention in circulation, e.g., in blood, serum, or other tissues, e.g., by at least 1.5, 2, 5, 10, or 50 fold. The modified blocking agent can be evaluated to assess whether it can reach sites of inflammation, e.g., joints.

For example, the TWEAK blocking agent (e.g., an antibody or soluble TWEAK-R protein) can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, a TWEAK blocking agent or TNF-α blocking agent can be conjugated to a water soluble polymer, e.g., a hydrophilic polyvinyl polymer, e.g., polyvinylalcohol or polyvinylpyrrolidone. A non-limiting list of such polymers includes polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

When the TWEAK blocking agent (e.g., an antibody or soluble TWEAK-R protein) is used in combination with a second agent (e.g., a TNF-α blocking agent or other agent described herein), the two agents can be formulated separately or together. For example, the respective pharmaceutical compositions can be mixed, e.g., just prior to administration, and administered together or can be administered separately, e.g., at the same or different times.

Other therapeutic agents described herein can also be provided as pharmaceutical composition, e.g., by standard methods or method described herein.

Administration

The TWEAK blocking agent (e.g., an antibody or soluble TWEAK-R protein) and a TNF-α blocking agent can be administered to a subject, e.g., a human subject, by a variety of methods. For many applications, the route of administration is one of: intravenous injection or infusion (IV), subcutaneous injection (SC), intraperitoneally (IP), or intramuscular injection. It is also possible to use intra-articular delivery. In some cases, administration may be directly to a site of inflammation, e.g., a joint or other inflamed site. The blocking agent can be administered as a fixed dose, or in a mg/kg dose.

The dose can also be chosen to reduce or avoid production of antibodies against the TWEAK blocking agent.

The route and/or mode of administration of the blocking agent can also be tailored for the individual case, e.g., by monitoring the subject, e.g., using tomographic imaging, neurological exam, and standard parameters associated with the particular disorder, e.g., criteria for assessing rheumatoid arthritis.

Dosage regimens are adjusted to provide the desired response, e.g., a therapeutic response or a combinatorial therapeutic effect. Generally, any combination of doses (either separate or co-formulated) of the TWEAK blocking agent (e.g., an antibody) (and optionally a second agent, e.g., a TNF-α blocking agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, or 1-10 mg/kg can be administered. Other doses can also be used.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the blocking agent may be administered via continuous infusion.

The TWEAK blocking agent can be administered, e.g., once or twice daily, or about one to four times per week, or preferably weekly, biweekly, or monthly, e.g., for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments. Animal models can also be used to determine a useful dose, e.g., an initial dose or a regimen.

If a subject is at risk for developing an inflammatory disorder or other disorder described herein, the blocking agent can be administered before the full onset of the disorder, e.g., as a preventative measure. The duration of such preventative treatment can be a single dosage of the blocking agent or the treatment may continue (e.g., multiple dosages). For example, a subject at risk for the disorder or who has a predisposition for the disorder may be treated with the blocking agent for days, weeks, months, or even years so as to prevent the disorder from occurring or fulminating.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

Devices and Kits for Therapy

Pharmaceutical compositions that include the TWEAK blocking agent (e.g., an antibody or soluble TWEAK-R) can be administered with a medical device. The device can designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include TWEAK blocking agent, and can be configured to deliver one or more unit doses of the blocking agent. The device can be further configured to administer a second agent, e.g., a TNF-α blocking agent, either as a single pharmaceutical composition that also includes the TWEAK blocking agent or as two separate pharmaceutical compositions.

For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering agents through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

A TWEAK blocking agent (e.g., an antibody or soluble TWEAK-R protein) can be provided in a kit. In one embodiment, the kit includes (a) a container that contains a composition that includes a TWEAK blocking agent, and optionally (b) informational material. The informational material can be descriptive, instructional, marketing or other material that relates to the methods described herein and/or the use of the agents for therapeutic benefit.

In an embodiment, the kit also includes a second agent for treating an inflammatory disorder, e.g., a TNF-α blocking agent. For example, the kit includes a first container that contains a composition that includes the TWEAK blocking agent, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the TWEAK blocking agent (e.g., an antibody or soluble TWEAK-R protein) and/or TNF-α blocking agent, e.g., in a suitable dose, dosage form, or mode of administration (e.g., a dose, dosage form, or mode of administration described herein), to treat a subject who has had or who is at risk for an inflammatory disorder, or other disorder described herein. The information can be provided in a variety of formats, include printed text, computer readable material, video recording, or audio recording, or information that provides a link or address to substantive material.

In addition to the blocking agent, the composition in the kit can include other ingredients, such as a solvent or buffer, a stabilizer, or a preservative. The blocking agent can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the TWEAK blocking agent and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Nucleic Acid and Protein Analysis

Numerous methods for detecting TWEAK or TWEAK-R protein and nucleic acid as well as proteins and nucleic acids for other biomarkers described herein (including those listed in Table 1) are available to the skilled artisan, including antibody-based methods for protein detection (e.g., Western blot or ELISA), and hybridization-based methods for nucleic acid detection (e.g., PCR or Northern blot).

Arrays are particularly useful molecular tools for characterizing a sample, e.g., a sample from a subject. For example, an array having capture probes for multiple genes, including probes for TWEAK and/or other biomarkers, or for multiple proteins, can be used in a method described herein. Altered expression of TWEAK (or other biomarker provided herein) nucleic acids and/or protein can be used to evaluate a sample, e.g., a sample from a subject, e.g., to evaluate a disorder described herein.

Arrays can have many addresses, e.g., locatable sites, on a substrate. The featured arrays can be configured in a variety of formats, non-limiting examples of which are described below. The substrate can be opaque, translucent, or transparent. The addresses can be distributed, on the substrate in one dimension, e.g., a linear array; in two dimensions, e.g., a planar array; or in three dimensions, e.g., a three dimensional array. The solid substrate may be of any convenient shape or form, e.g., square, rectangular, ovoid, or circular.

Arrays can be fabricated by a variety of methods, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin based methods (e.g., as described in U.S. Pat. No. 5,288,514), and bead based techniques (e.g., as described in PCT US/93/04145).

The capture probe can be a single-stranded nucleic acid, a double-stranded nucleic acid (e.g., which is denatured prior to or during hybridization), or a nucleic acid having a single-stranded region and a double-stranded region. Preferably, the capture probe is single-stranded. The capture probe can be selected by a variety of criteria, and preferably is designed by a computer program with optimization parameters. The capture probe can be selected to hybridize to a sequence rich (e.g., non-homopolymeric) region of the gene. The $T_m$ of the capture probe can be optimized by prudent selection of the complementarity region and length. Ideally, the $T_m$ of all capture probes on the array is similar, e.g., within 20, 10, 5, 3, or 2° C. of one another.

The isolated nucleic acid is preferably mRNA that can be isolated by routine methods, e.g., including DNase treatment to remove genomic DNA and hybridization to an oligo-dT coupled solid substrate (e.g., as described in *Current Protocols in Molecular Biology*, John Wiley & Sons, N.Y). The substrate is washed, and the mRNA is eluted.

The isolated mRNA can be reversed transcribed and optionally amplified, e.g., by rtPCR, e.g., as described in (U.S. Pat. No. 4,683,202). The nucleic acid can be an amplification product, e.g., from PCR (U.S. Pat. Nos. 4,683,196 and 4,683,202); rolling circle amplification ("RCA," U.S. Pat. No. 5,714,320), isothermal RNA amplification or NASBA (U.S. Pat. Nos. 5,130,238; 5,409,818; and 5,554,517), and strand displacement amplification (U.S. Pat. No. 5,455,166). The nucleic acid can be labeled during amplification, e.g., by the incorporation of a labeled nucleotide. Examples of preferred labels include fluorescent labels, e.g., red-fluorescent dye Cy5 (Amersham) or green-fluorescent dye Cy3 (Amersham), and chemiluminescent labels, e.g., as described in U.S. Pat. No. 4,277,437. Alternatively, the nucleic acid can be labeled with biotin, and detected after hybridization with labeled streptavidin, e.g., streptavidin-phycoerythrin (Molecular Probes).

The labeled nucleic acid can be contacted to the array. In addition, a control nucleic acid or a reference nucleic acid can be contacted to the same array. The control nucleic acid or reference nucleic acid can be labeled with a label other than the sample nucleic acid, e.g., one with a different emission maximum. Labeled nucleic acids can be contacted to an array under hybridization conditions. The array can be washed, and then imaged to detect fluorescence at each address of the array.

The expression level of a TWEAK or other biomarker can be determined using an antibody specific for the polypeptide (e.g., using a western blot or an ELISA assay). Moreover, the expression levels of multiple proteins, including TWEAK and the exemplary biomarkers provided herein, can be rapidly determined in parallel using a polypeptide array having antibody capture probes for each of the polypeptides. Antibodies specific for a polypeptide can be generated by a method described herein (see "Antibody Generation"). The expression level of a TWEAK and the exemplary biomarkers provided herein can be measured in a subject (e.g., in vivo imaging) or in a biological sample from a subject (e.g., blood, serum, plasma, or synovial fluid).

A low-density (96 well format) protein array has been developed in which proteins are spotted onto a nitrocellulose membrane (Ge (2000) *Nucleic Acids Res.* 28, e3, I-VII). A high-density protein array (100,000 samples within 222×222 mm) used for antibody screening was formed by spotting proteins onto polyvinylidene difluoride (PVDF) (Lueking et al. (1999) *Anal. Biochem.* 270:103-111). See also, e.g., Mendoza et al. (1999). *Biotechniques* 27:778-788; MacBeath and Schreiber (2000) *Science* 289:1760-1763; and De Wildt et al. (2000) *Nature Biotech.* 18:989-994. These art-known methods and other can be used to generate an array of antibodies for detecting the abundance of polypeptides in a sample. The sample can be labeled, e.g., biotinylated, for subsequent detection with streptavidin coupled to a fluorescent label. The array can then be scanned to measure binding at each address.

The nucleic acid and polypeptide arrays of the invention can be used in a wide variety of applications. For example, the arrays can be used to analyze a patient sample. The sample is compared to data obtained previously, e.g., known clinical specimens or other patient samples. Further, the arrays can be used to characterize a cell culture sample, e.g., to determine a cellular state after varying a parameter, e.g., exposing the cell culture to an antigen, a transgene, or a test compound.

The expression data can be stored in a database, e.g., a relational database such as a SQL database (e.g., Oracle or Sybase database environments). The database can have multiple tables. For example, raw expression data can be stored in one table, wherein each column corresponds to a gene being assayed, e.g., an address or an array, and each row corresponds to a sample. A separate table can store identifiers and sample information, e.g., the batch number of the array used, date, and other quality control information.

Expression profiles obtained from gene expression analysis on an array can be used to compare samples and/or cells in a variety of states as described in Golub et al. ((1999) *Science* 286:531). In one embodiment, expression (e.g., mRNA expression or protein expression) information for a gene encoding TWEAK and/or a gene encoding a exemplary biomarker provided herein are evaluated, e.g., by comparison a reference value, e.g., a reference value. Reference values can be obtained from a control, e.g., a reference subject. Reference values can also be obtained from statistical analysis, e.g., to provide a reference value for a cohort of subject, e.g., age and gender matched subject, e.g., normal subjects or subject who have rheumatoid arthritis or other disorder described herein. Statistical similarity to a particular reference (e.g., to a reference for a risk-associated cohort) or a normal cohort can be used to provide an assessment (e.g., an indication of risk of inflammatory disorder) to a subject, e.g., a subject who has not been diagnosed with a disorder described herein.

Subjects suitable for treatment can also be evaluated for expression and/or activity of TWEAK and/or other biomarker. Subjects can be identified as suitable for treatment (e.g., with a TWEAK blocking agent), if the expression and/or activity for TWEAK and/or the other biomarker is elevated relative to a reference, e.g., reference value, e.g., a reference value associated with normal.

Subjects who are being administered an agent described herein or other treatment can be evaluated as described for expression and/or activity of TWEAK and/or other biomarkers described herein. The subject can be evaluated at multiple times. e.g., at multiple times during a course of therapy, e.g., during a therapeutic regimen. Treatment of the subject can be modified depending on how the subject is responding to the therapy. For example, a reduction in TWEAK expression or activity or a reduction in the expression or activity of genes stimulated by TWEAK can be indicative of responsiveness.

Particular effects mediated by an agent may show a difference (e.g., relative to an untreated subject, control subject, or other reference) that is statistically significant (e.g., P value<0.05 or 0.02). Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02.

Methods of Evaluating Genetic Material

There are numerous methods for evaluating genetic material to provide genetic information. These methods can be used to evaluate a genetic locus that includes a gene encoding TWEAK or a gene encoding a biomarker described herein. The methods can be used to evaluate one or more nucleotides, e.g., a coding or non-coding region of the gene, e.g., in a regulatory region (e.g., a promoter, a region encoding an untranslated region or intron, and so forth).

Nucleic acid samples can analyzed using biophysical techniques (e.g., hybridization, electrophoresis, and so forth), sequencing, enzyme-based techniques, and combinations-thereof. For example, hybridization of sample nucleic acids to nucleic acid microarrays can be used to evaluate sequences in an mRNA population and to evaluate genetic polymorphisms. Other hybridization based techniques include sequence specific primer binding (e.g., PCR or LCR); Southern analysis of DNA, e.g., genomic DNA; Northern analysis of RNA, e.g., mRNA; fluorescent probe based techniques (see, e.g., Beaudet et al. (2001) *Genome Res.* 11(4):600-8); and allele specific amplification. Enzymatic techniques include restriction enzyme digestion; sequencing; and single base extension (SBE). These and other techniques are well known to those skilled in the art.

Electrophoretic techniques include capillary electrophoresis and Single-Strand Conformation Polymorphism (SSCP) detection (see, e.g., Myers et al. (1985) *Nature* 313:495-8 and Ganguly (2002) *Hum Mutat.* 19(4):334-42). Other biophysical methods include denaturing high pressure liquid chromatography (DHPLC).

In one embodiment, allele specific amplification technology that depends on selective PCR amplification may be used to obtain genetic information. Oligonucleotides used as primers for specific amplification may carry the mutation of interest in the center of the molecule (so that amplification depends on differential hybridization) (Gibbs et al. (1989) *Nucl. Acids Res.* 17:2437-2448) or at the extreme 3' end of one primer where, under appropriate conditions, mismatch can prevent, or reduce polymerase extension (Prossner (1993) *Tibtech* 11:238). In addition, it is possible to introduce a restriction site in the region of the mutation to create cleavage-based detection (Gasparini et al. (1992) *Mol. Cell Probes* 6:1). In another embodiment, amplification can be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Enzymatic methods for detecting sequences include amplification based-methods such as the polymerase chain reaction (PCR; Saiki, et al. (1985) *Science* 230:1350-1354) and ligase chain reaction (LCR; Wu. et al. (1989) *Genomics* 4:560-569; Barringer et al. (1990), *Gene* 1989:117-122; F. Barany (1991) *Proc. Natl. Acad. Sci. USA* 1988:189-193); transcription-based methods utilize RNA synthesis by RNA polymerases to amplify nucleic acid (U.S. Pat. Nos. 6,066,457; 6,132,997; and 5,716,785; Sarkar et al., (1989) *Science* 244:331-34; Stofler et al., (1988) *Science* 239:491); NASBA (U.S. Pat. Nos. 5,130,238; 5,409,818; and 5,554,517); rolling circle amplification (RCA; U.S. Pat. Nos. 5,854,033 and 6,143,495) and strand displacement amplification (SDA; U.S. Pat. Nos. 5,455,166 and 5,624,825). Amplification methods can be used in combination with other techniques.

Other enzymatic techniques include sequencing using polymerases, e.g., DNA polymerases and variations thereof such as single base extension technology. See, e.g., U.S. Pat. Nos. 6,294,336; 6,013,431; and 5,952,174.

Fluorescence based detection can also be used to detect nucleic acid polymorphisms. For example, different terminator ddNTPs can be labeled with different fluorescent dyes. A primer can be annealed near or immediately adjacent to a polymorphism, and the nucleotide at the polymorphic site can be detected by the type (e.g., "color") of the fluorescent dye that is incorporated.

Hybridization to microarrays can also be used to detect polymorphisms, including SNPs. For example, a set of different oligonucleotides, with the polymorphic nucleotide at varying positions with the oligonucleotides can be positioned on a nucleic acid array. The extent of hybridization as a function of position and hybridization to oligonucleotides specific for the other allele can be used to determine whether a particular polymorphism is present. See, e.g., U.S. Pat. No. 6,066,454.

In one implementation, hybridization probes can include one or more additional mismatches to destabilize duplex formation and sensitize the assay. The mismatch may be directly adjacent to the query position, or within 10, 7, 5, 4, 3, or 2 nucleotides of the query position. Hybridization probes can also be selected to have a particular $T_m$, e.g., between 45-60° C., 55-65° C., or 60-75° C. In a multiplex assay, $T_m$'s can be selected to be within 5, 3, or 2° C. of each other.

It is also possible to directly sequence the nucleic acid for a particular genetic locus, e.g., by amplification and sequencing, or amplification, cloning and sequence. High throughput automated (e.g., capillary or microchip based) sequencing apparati can be used. In still other embodiments, the sequence of a protein of interest is analyzed to infer its genetic sequence. Methods of analyzing a protein sequence include protein sequencing, mass spectroscopy, sequence/epitope specific immunoglobulins, and protease digestion.

Any combination of the above methods can also be used. The above methods can be used to evaluate any genetic locus, e.g., in a method for analyzing genetic information from particular groups of individuals or in a method for analyzing a polymorphism associated with a disorder described herein, e.g., rheumatoid arthritis, e.g., in a gene encoding TWEAK or another biomarker described herein.

EXAMPLES

Example 1

Exemplary Sequences

An exemplary sequence of a human TWEAK protein is as follows

```
                                            (SEQ ID NO: 1)
MAARRSQRRR GRRGEPGTAL LVPLALGLGL ALACLGLLLA

VVSLGSRASL SAQEPAQEEL VAEEDQDPSE LNPQTEESQD

PAPFLNRLVR PRRSAPKGRK TRARRAIAAH YEVHPRPGQD

GAQAGVDGTV SGWEEARINS SSPLRYNRQI GEFIVTRAGL

YYLYCQVHFD EGKAVYLKLD LLVDGVLALR CLEEFSATAA

SSLGPQLRLC QVSGLLALRP GSSLRIRTLP WAHLKAAPFL

TYFGLFQVH
```

An exemplary sequence of a human Fn14 protein is as follows:

```
                                            (SEQ ID NO: 2)
MARGSLRRLL RLLVLGLWLA LLRSVAGEQA PGTAPCSRGS

SWSADLDKCM DCASCRARPH SDFCLGCAAA PPAPFRLLWP

ILGGALSLTF VLGLLSGFLV WRRCRRREKF TTPIEETGGE

GCPAVALIQ
```

Example 2

Genes that are Synergistically Activated by TWEAK and TNF-α

Microarrays were analyzed to identify genes whose expression in human synoviocytes was induced by TWEAK and TNF-α. The following are examples of genes that are synergistically activated by TWEAK and TNF-α.

TABLE 1

| Genes Synergistically Activated by TWEAK and TNF-α | |
|---|---|
| AffyID | annotation |
| 208229_at | — |
| 216064_s_at | — |
| 220396_at | — |
| 222332_at | — |
| 207999_s_at | adenosine deaminase, RNA-specific, B1 (RED1 homolog rat) |

TABLE 1-continued

Genes Synergistically Activated by TWEAK and TNF-α

| | |
|---|---|
| 202109_at | ADP-ribosylation factor interacting protein 2 (arfaptin 2) |
| 201444_s_at | ATPase, H+ transporting, lysosomal accessory protein 2 |
| 210538_s_at | baculoviral IAP repeat-containing 3 |
| 221534_at | basophilic leukemia expressed protein BLES03 |
| 203773_x_at | biliverdin reductase A |
| 205733_at | Bloom syndrome |
| 211314_at | calcium channel, voltage-dependent, alpha 1G subunit |
| 217118_s_at | chromosome 22 open reading frame 9 |
| 216607_s_at | cytochrome P450, family 51, subfamily A, polypeptide 1 |
| 213279_at | dehydrogenase/reductase (SDR family) member 1 |
| 209703_x_at | DKFZP586A0522 protein |
| 210839_s_at | ectonucleotide pyrophosphatase/phosphodiesterase 2 (autotaxin) |
| 210002_at | GATA binding protein 6 |
| 212241_at | glutamate receptor, ionotropic, N-methyl D-aspartate-like 1A |
| 208055_s_at | hect domain and RLD 4 |
| 204512_at | human immunodeficiency virus type I enhancer binding protein 1 |
| 216510_x_at | immunoglobulin heavy constant gamma 1 (G1m marker) |
| 201548_s_at | Jumonji, AT rich interactive domain 1B (RBP2-like) |
| 220972_s_at | keratin associated protein 9-9 |
| 212805_at | KIAA0367 |
| 212546_s_at | KIAA0826 |
| 215680_at | KIAA1654 protein |
| 218906_x_at | likely ortholog of kinesin light chain 2 |
| 210104_at | mediator of RNA polymerase II transcription, subunit 6 homolog (yeast) |
| 214397_at | methyl-CpG binding domain protein 2 |
| 212713_at | microfibrillar-associated protein 4 |
| 203901_at | mitogen-activated protein kinase kinase kinase 7 interacting protein 1 |
| 213040_s_at | neuronal pentraxin receptor |
| 202783_at | nicotinamide nucleotide transhydrogenase |
| 211691_x_at | Ornithine decarboxylase antizyme 4 mRNA, complete cds |
| 205991_s_at | paired related homeobox 1 |
| 204715_at | pannexin 1 |
| 214735_at | phosphoinositide-binding protein PIP3-E |
| 203709_at | phosphorylase kinase, gamma 2 (testis) |
| 207709_at | protein kinase, AMP-activated, alpha 2 catalytic subunit |
| 213136_at | protein tyrosine phosphatase, non-receptor type 2 |
| 213524_s_at | putative lymphocyte G0/G1 switch gene |
| 202388_at | regulator of G-protein signalling 2, 24 kDa |
| 218441_s_at | RNA polymerase II associated protein 1 |
| 212140_at | SCC-112 protein |
| 201471_s_at | sequestosome 1 |
| 212609_s_at | serologically defined colon cancer antigen 8 |
| 212393_at | SET binding factor 1 |
| 214931_s_at | SFRS protein kinase 2 |
| M97935_MB_at | signal transducer and activator of transcription 1, 91 kDa |
| 204804_at | Sjogren syndrome antigen A1 (52 kDa, ribonucleoprotein autoantigen SS-A/Ro) |
| 214925_s_at | spectrin, alpha, non-erythrocytic 1 (alpha-fodrin) |
| 221268_s_at | sphingosine-1-phosphate phosphatase 1 |
| 212154_at | syndecan 2 (heparan sulfate proteoglycan 1, cell surface-associated, fibroglycan) |
| 212800_at | syntaxin 6 |
| 201449_at | TIA1 cytotoxic granule-associated RNA binding protein |
| 216241_s_at | transcription elongation factor A (SII), 1 |
| 201399_s_at | translocation associated membrane protein 1 |
| 210372_s_at | tumor protein D52-like 1 |
| 206959_s_at | UPF3 regulator of nonsense transcripts homolog A (yeast) |
| 219393_s_at | v-akt murine thymoma viral oncogene homolog 3 (protein kinase B, gamma) |
| 205205_at | v-rel reticuloendotheliosis viral oncogene homolog B, nuclear factor of kappa light polypeptide gene enhancer in B-cells 3 (avian) |

TABLE 1-continued

Genes Synergistically Activated by TWEAK and TNF-α

| Probe Set Id | Gene Title |
|---|---|
| 1405_i_at | Chemokine (C-C motif) ligand 5 (CCL5) |
| 204490_s_at | CD44 antigen (homing function and Indian blood group system) (CD44) |
| 204655_at | RANTES (SCYA5) |
| 205619_s_ay | mesenchyme homeo box 1 (MEOX1) platelet-derived growth factor receptor-like . . . (NM_006207) fibroblast growth factor receptor 4 fibroblast growth factor 22 chemokine (C-C motif) ligand 18 |

Still other genes are activated by both (i) TWEAK in the absence of TNF-α and (ii) TNF-α in the absence of TWEAK.

Example 3

Effect of Combination of Blocking TWEAK and TNF in mCIA as Measured by an Average Arthritis Index

The mouse collagen-induced arthritis (mCIA) model is a commonly-used model (see e.g., Stuart et al., *J. Clin. Invest.* 69:673-683 (1982)) of rheumatoid arthritis. A mCIA model was used to study the effects of a combination anti-TWEAK and anti-TNF-α treatment on arthritis development. Arthritis was induced in mice via collagen immunization (CII/CFA: collagen II and complete Freud's adjuvant). Anti-TWEAK monoclonal antibody (mu anti-TWEAK mAb+hu IgG1); soluble TNF-α receptor (TNFr-hu Fc+mu IgG2a); a combination of anti-TWEAK monoclonal antibody and soluble TNF-α receptor (mu anti-TWEAK mAb+TNFr-hu Fc); or PBS or isotype-matched negative controls were administered on days 20, 23, 27, 30, and 34 after collagen immunization. Each treatment group contained ten mice. Each antibody was administered at a dose of 10 mg/kg. Arthritis was assessed using an average arthritis index (see e.g., Li et al., *Arthritis Res. Ther.* 6:R273-R281 (2004)). Four paws were measured per mouse using the scoring system: 0=normal paw; 1=swelling of individual digits; 2=moderate swelling and redness of ankle or wrist joints; 3=swelling and redness of at least two joints; and 4=swelling of the whole paw. The sum of the four paw scores (y axis) were plotted against the days after collagen immunization (x axis).

FIG. 1 shows the results of this study. The mice treated with the combination of anti-TWEAK and anti-TNF-α agents had a lower average arthritis index score than mice treated with either blocking agent alone or the controls. Also, as indicated on the right side of the graph under "% incidence," the mice treated with the combination had a lower overall incidence of arthritis (60%) than mice treated with either agent alone (67% for anti-TNF-α treatment; 80% for anti-TWEAK mAb treatment) or with the controls (80% for PBS treatment; 90% for isotype matched antibody treatment).

Example 4

Effect of Combination of Blocking TWEAK and TNF in mCIA as Measured by Average Metatarsal Height

The mCIA model was used to study the effects of a combination anti-TWEAK and anti-TNF-α therapy on arthritis development as measured by average metatarsal height/paw thickness (see e.g., Campo et al., *Arthritis Res. Ther.* 5:R122-R131 (2003)).

Mice were treated with anti-TWEAK monoclonal antibody (mu anti-TWEAK mAb+hu IgG1); soluble TNF-α receptor (TNFRp55:hu Fc+mu IgG2a); a combination of anti-TWEAK monoclonal antibody and soluble TNF-α receptor (mu anti-TWEAK mAb+TNFRp55:hu Fc); or PBS or isotype-matched negative controls on days 20, 23, 27, 30, and 34 after collagen immunization. Each treatment group contained ten mice. Each antibody was administered at a dose of 10 mg/kg. Metatarsal height was measured using calipers 38 days after collagen immunization. The average metatarsal height (y axis) for each mouse per treatment (x axis) was plotted.

Figure 2:
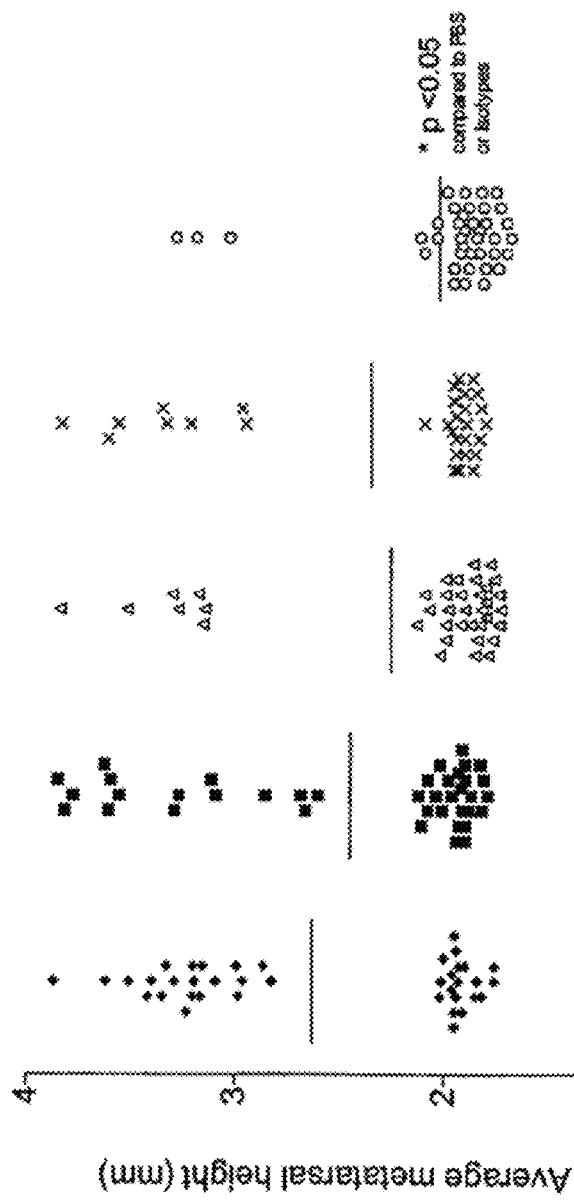
FIG. 2 is a plot showing average metatarsal height values in a mCIA model of arthritis in mice that were treated with a combination of TWEAK and TNF-α blocking agents, a TWEAK blocking agent alone, a TNF-α blocking agent alone, a PBS control, or isotype-matched controls.

FIG. 2 shows the results of this study. Mice treated with the combination of anti-TWEAK and anti-TNF-α agents had statistically-significant lower average metatarsal height values than mice treated with either blocking agent alone or the controls (*p<0.05 for the average value per treatment when compared to the controls).

Example 5

Effect of Combination of Blocking TWEAK and TNF in mCIA as Measured by Body Weight Change The mCIA model was used to study the effects of a combination anti-TWEAK and anti-TNF-α therapy on arthritis development as measured by percent body weight change (Campo et al., *Arthritis Res. Ther.* 5:R122-R131 (2003)). Mice were treated with anti-TWEAK monoclonal antibody (mu anti-TWEAK mAb+hu IgG1 (an isotype matched control for TNFRp55:hu Fc)); soluble TNF-α receptor (TNFRp55:hu Fc+mu IgG2a); a combination of anti-TWEAK monoclonal antibody and soluble TNF-α receptor (mu anti-TWEAK mAb+TNFRp55:hu Fc); or PBS or isotype-matched negative controls on days 20, 23, 27, 30, and 34 after collagen immunization. Each treatment group contained ten mice. Each antibody was administered at a dose of 10 mg/kg. Mice were weighed at various time points after collagen immunization and the percent change in body weight were calculated per treatment. The percent body weight change for each treatment (y axis) was plotted against the days after arthritis induction by collagen immunization (x axis).

Figure 3:
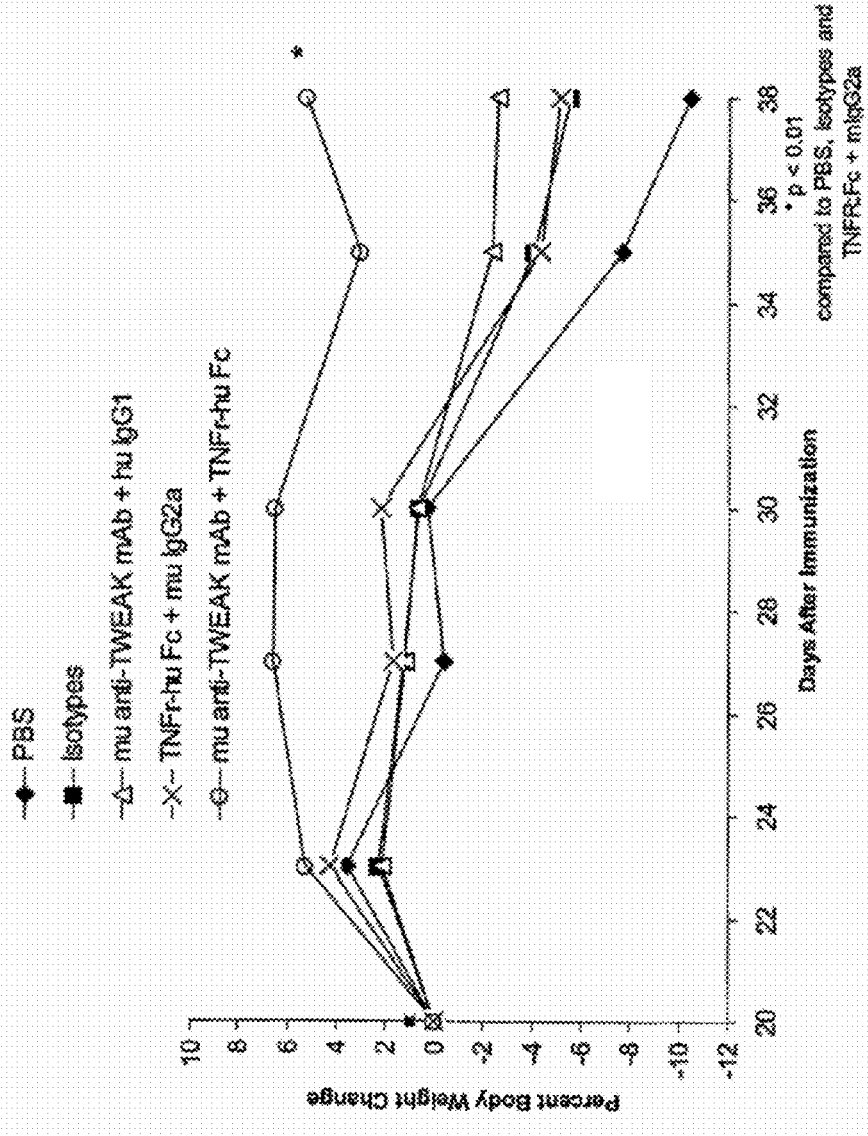
FIG. 3 is a line graph showing percent body weight change in a mCIA model of arthritis in mice that were treated with a combination of TWEAK and TNF-α blocking agents, a TWEAK blocking agent alone, a TNF-α blocking agent alone, a PBS control, or isotype-matched controls.

FIG. 3 shows the results of this study. Mice treated with the combination of anti-TWEAK and anti-TNF-α agents had a statistically-significant smaller percent change in body weight than mice treated with either blocking agent alone or the controls (*p<0.01 for the value per treatment when compared to the controls or to the TNFRp55:hu Fc+mu IgG2a treated mice).

Example 6

TWEAK Induced Genes

We applied TWEAK doses (5 ng/ml and 50 ng/ml) to cells at both 6 and 24 hour time points, and observed that some genes are modulated by TWEAK only. These genes were not affected by application of TNF-α, even at a concentration of 5 ng/ml. Examples of such genes are:

TABLE 2

1. NIK/mitogen-activated protein kinase kinase kinase 14(MAP3K14)
2. *Homo sapiens* cDNA FLJ11796 fis, clone HEMBA1006158, highly similar to *Homo sapiens* transcription factor forkhead-like 7 (FKHL7) gene TABLE 2-continued 3. similar to glucosamine-6-sulfatases *Homo sapiens* serum glucocorticoid regulated kinase (SGK), mRNA
4. *Homo sapiens* REV3 (yeast homolog)-like, catalytic subunit of DNA polymerase zeta (REV3L), mRNA.
5. ADAM 10/a disintegrin and metalloproteinase domain 10
6. nuclear factor (erythroid-derived 2)-like 1
7. *Homo sapiens* SerArg-related nuclear matrix protein (plenty of prolines 101-like) (SRM160), mRNA.
8. *Homo sapiens* doublecortin and CaM kinase-like 1 (DCAMKL1), mRNA.
9. *Homo sapiens* Cdc42 effector protein 4; binder of Rho GTPases 4 (CEP4), mRNA.
10. *Homo sapiens* mRNA; cDNA DKFZp762L106 (from clone DKFZp762L106); partial cds.

In addition, in normal human synoviocytes, CBR3 and IL8 are induced by TWEAK treatment (5 ng/ml) alone.

Example 7

Experiments with TWEAK

Figure 4:
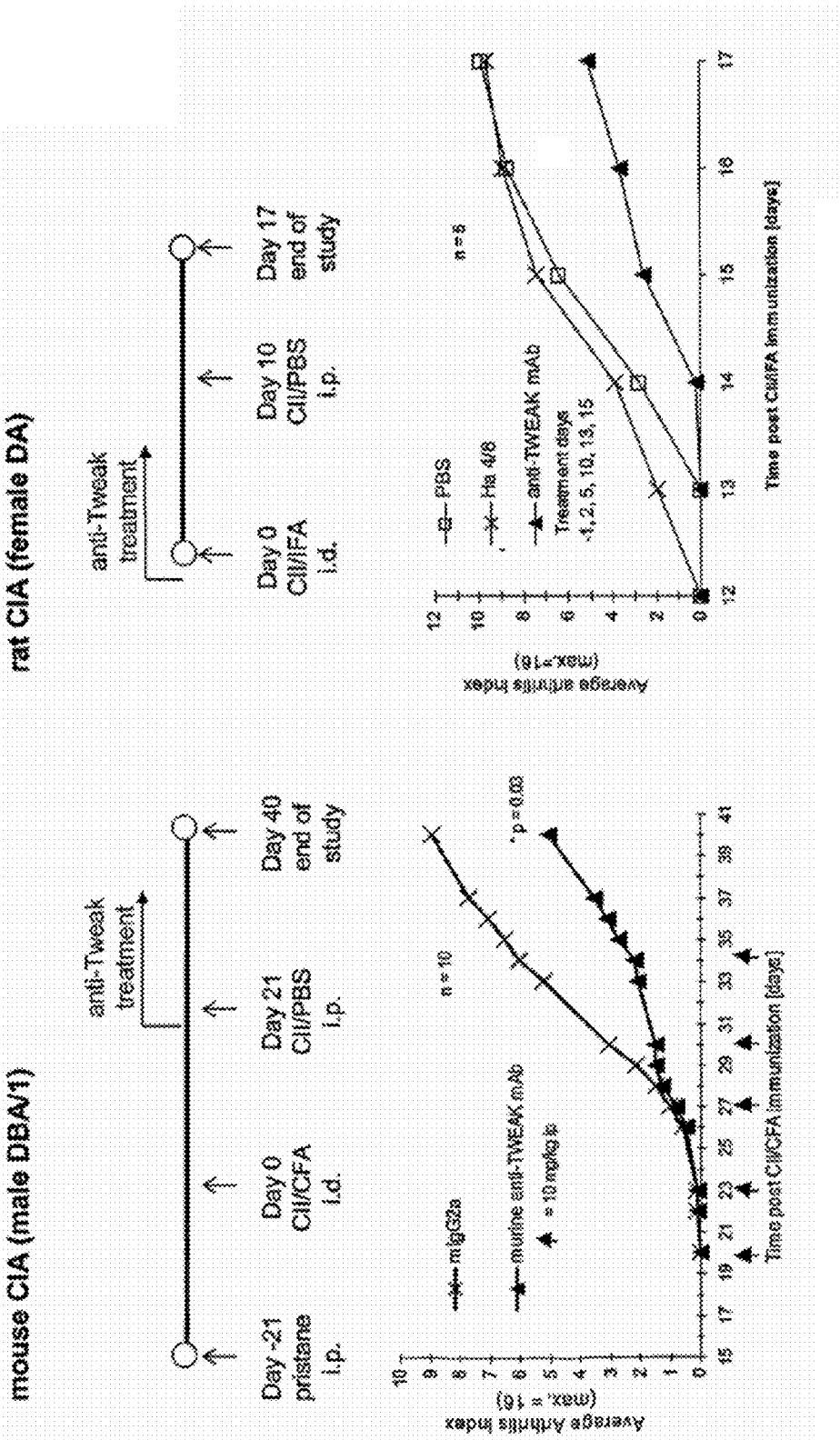
FIG. 4 depicts two line plots showing average arthritis index values in CIA models of arthritis in animals treated with anti-TWEAK blocking antibodies (anti-TWEAK mAbs) or controls. The left panel shows results obtained using a mouse CIA model; the right panel shows results obtained using a rat CIA model.

FIG. 4 shows that treatment with TWEAK-blocking monoclonal antibodies can lessen the development of arthritis in both mouse and rat CIA models of arthritis. The left panel shows that treatment with an anti-TWEAK antibody (murine anti-TWEAK mAb) results in a lower value in the average arthritis index, as compared to treatment with a control antibody (mIgG2a), in a mouse CIA model in which arthritis was induced with CII/CFA. The right panel shows that treatment with an anti-TWEAK antibody (anti-TWEAK mAb) results in a lower value in the average arthritis index, as compared to treatment with a control antibody (Ha 4/8) or PBS in a rat CIA model, in which arthritis was induced with collagen II and incomplete Freud's adjuvant (CII/IFA).

Figure 5:
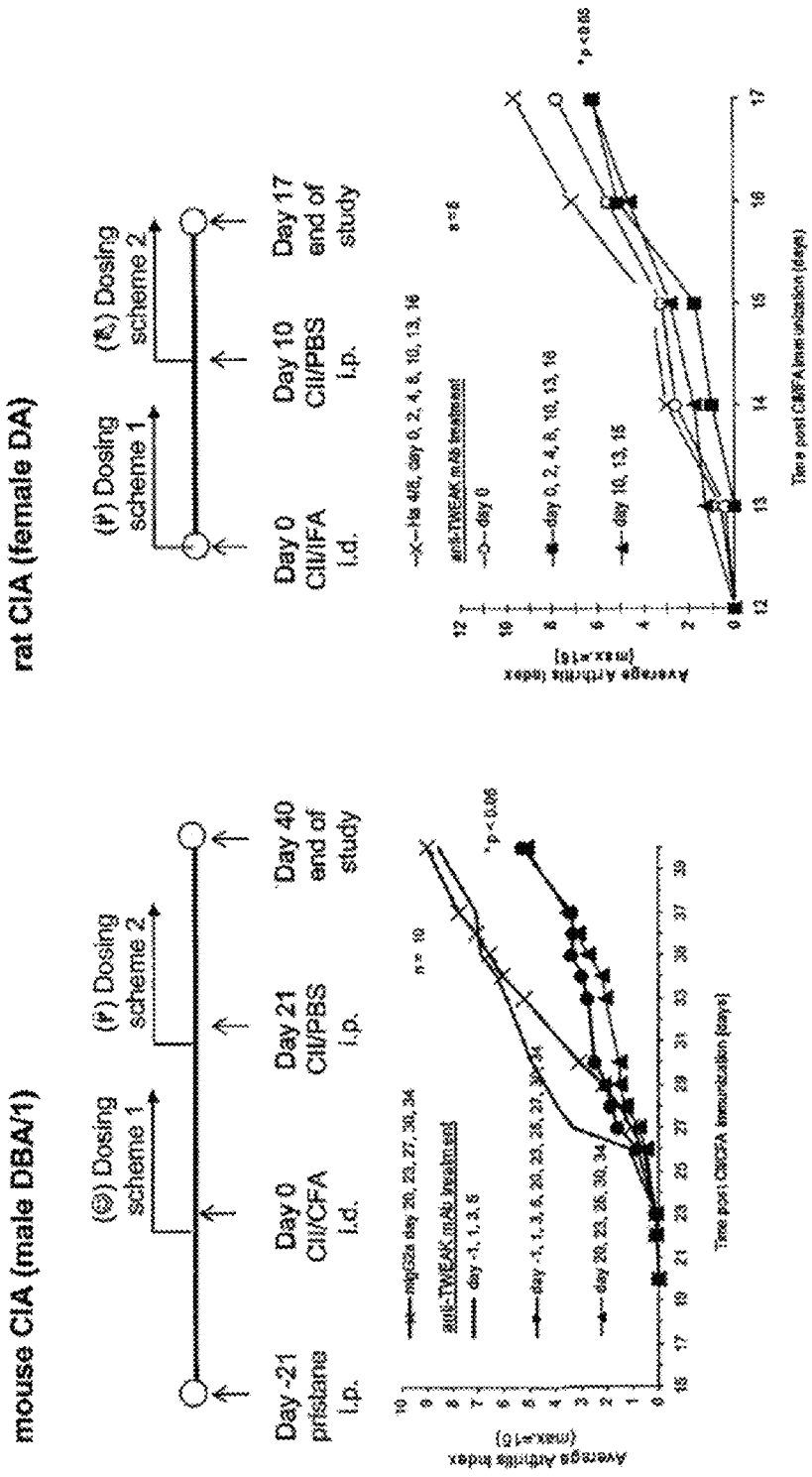
FIG. 5 depicts two line plots showing average arthritis index values in CIA models of arthritis in animals treated with anti-TWEAK blocking antibodies (anti-TWEAK mAbs) or controls. The figures show the results of two dosing regimens: in the first, the antibody is administered at the time of arthritis induction, in the second, the antibody is administered after arthritis induction. The left panel shows results obtained using a mouse CIA model; the right panel shows results obtained using a rat CIA model.

FIG. 5 shows that TWEAK-blocking monoclonal antibodies can be administered at the same time as (Dosing scheme 1) or after (Dosing scheme 2) the induction of arthritis by collagen immunization and still have the effect of lessening the development of arthritis in both mouse and rat CIA models of arthritis. The left panel shows that an anti-TWEAK antibody can be administered prior to or after the induction of arthritis to effect a lower value in the average arthritis index, as compared to administration of a control antibody (mIgG2a), in a mouse CIA model. The right panel shows that an anti-TWEAK antibody can be administered prior to or after the induction of arthritis to effect a lower value in the average arthritis index, as compared to administration of a control antibody (Ha 4/8) or PBS, in a rat CIA model.

Figure 6:
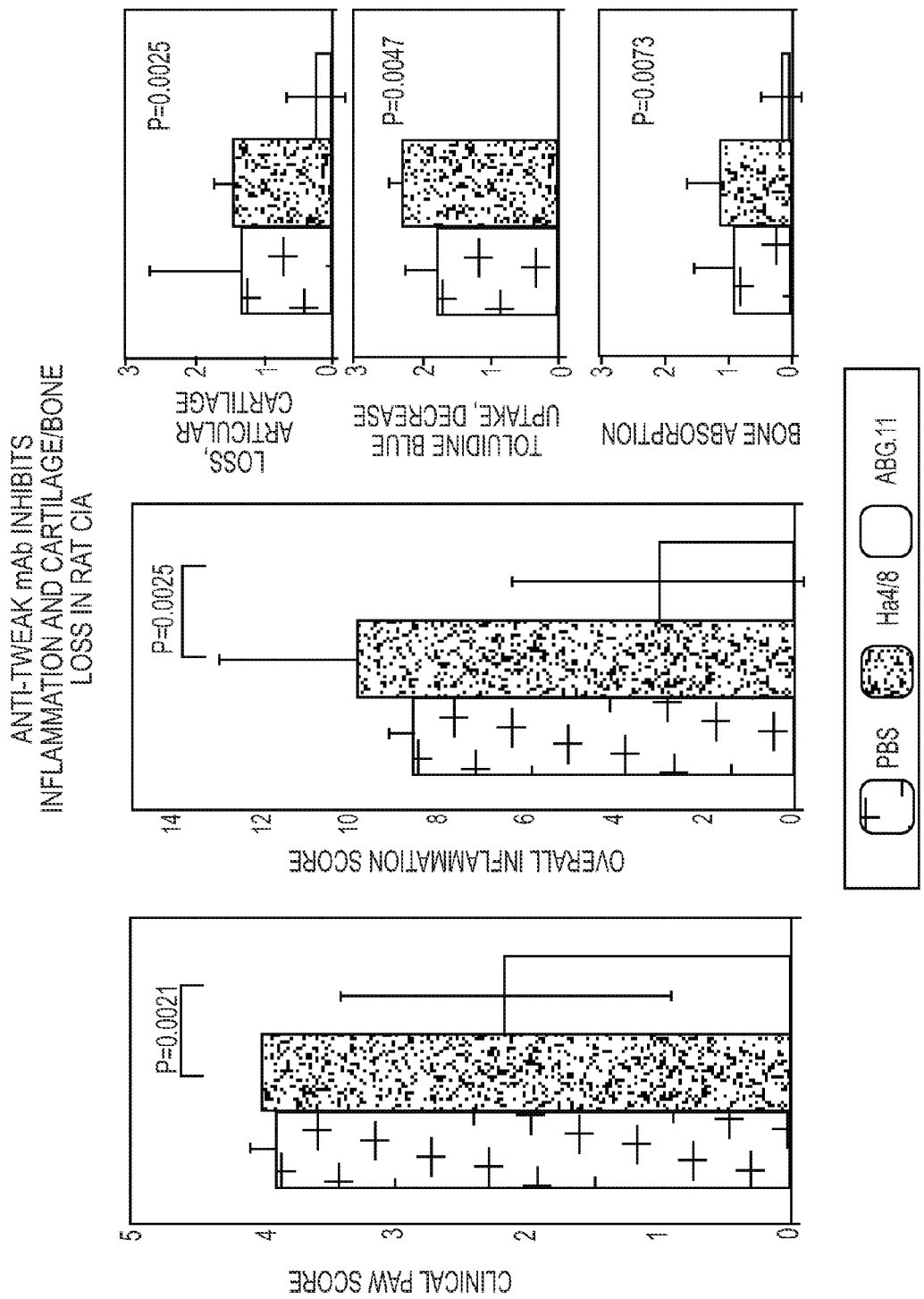
FIG. 6 includes five bar graphs showing levels of inflammation and cartilage and bone loss in a rat CIA model of arthritis in rats treated with anti-TWEAK blocking antibodies (ABG.11) or controls. Similarly findings can be observed in a mouse model.

FIG. 6 shows that anti-TWEAK monoclonal antibody (ABG. 11) treatment decreases inflammation in the rat CIA model, as measured by a clinical paw score and an overall inflammation score; the treatment also decreases cartilage and bone loss, as measured by the parameters of bone absorption, decrease in toluidine blue uptake, and loss of articular cartilage. Similar results were seen in the mouse CIA model.

Figure 7:
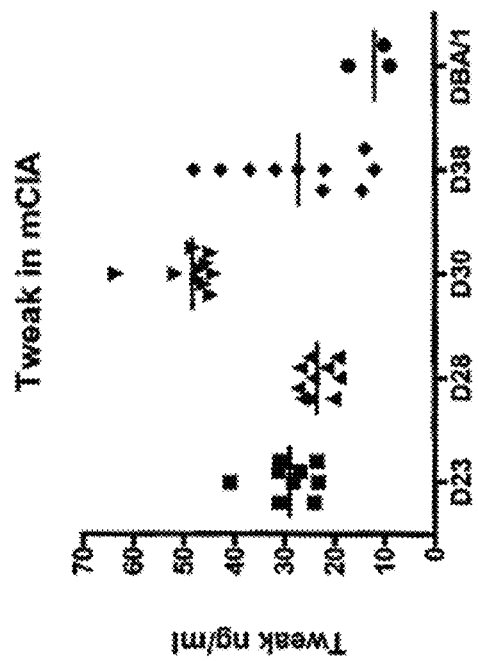
FIG. 7 is a plot showing serum TWEAK levels at various time points after induction of arthritis in a mCIA model and in a control mouse (DBA/1).

FIG. 7 shows serum TWEAK levels in the mouse CIA model at various time points (day (D) 23, 28, 30, and 38) after induction of arthritis. TWEAK levels were elevated as compared to the levels in control mice (DBA/1).

Figure 8:
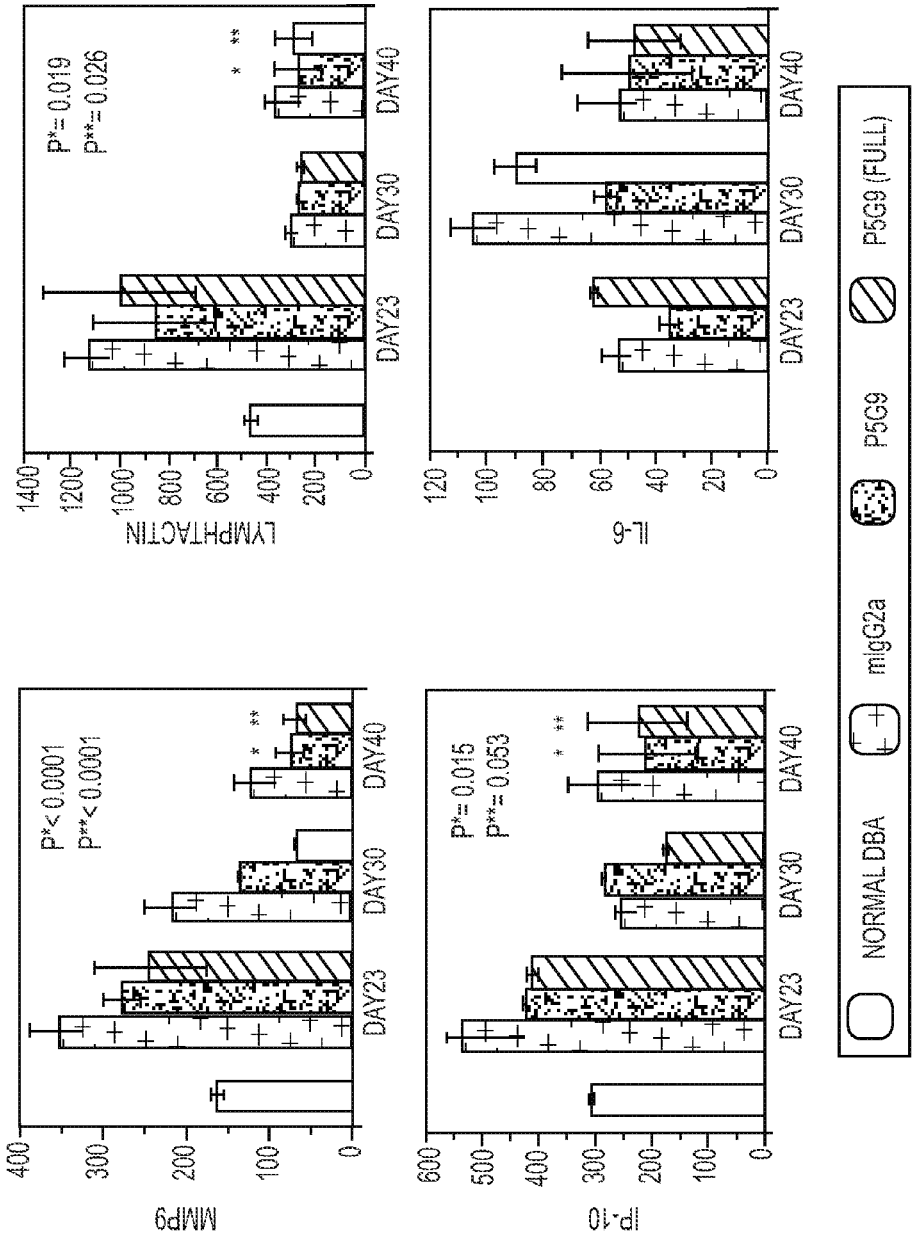
FIG. 8 includes four bar graphs showing the levels of MMP9, lymphotactin, IP-10, and IL-6 at various time points after induction of arthritis in the mCIA model in mice treated with anti-TWEAK blocking antibodies (P5G9 and P5G9 (Full)) or controls.

FIG. 8 shows the levels of MMP9, lymphotactin, IP-10, and IL-6 at various time points (day 23, 30, and 40) after induction of arthritis in the mouse CIA model. Treatment with anti-TWEAK monoclonal antibody (P5G9 and P5G9 (Full, also termed dosing scheme 1)) prevented as great an increase in the levels of these proteins, as compared to the levels in mice treated with a control (mIgG2a) or in mice not immunized to develop arthritis (normal DBA). Similar results were seen in the rat CIA model.

Experiments were performed to demonstrate that inhibition of TWEAK with anti-TWEAK antibodies does not affect the adaptive immune response. After collagen immunization, mice that had been treated with anti-TWEAK monoclonal antibodies were able to mount collagen-specific B cell and T cell responses to a similar extent as mice that had been treated with a control, isotype-matched antibody (mIgG2a; data not shown).

Experiments were performed to measure the levels of Fn14 (TWEAK receptor) on primary human cell types found in a joint: fibroblast-like synoviocytes, articular chondrocytes, and osteoblasts. Fluorescence-activated cell sorting experiments using anti-Fn14 antibody (ITEM-4) or a control antibody (anti-mFc) demonstrated that Fn14 levels were elevated above background in all three cells types, with levels being higher in the synoviocytes and osteoblasts than in the chondrocytes.

Experiments were performed to demonstrate that TWEAK and TNF-α can each stimulate matrix metalloprotease production by chondrocytes. MMP-1, MMP-2, MMP-3, and MMP-9 levels all increased after treatment with TWEAK (100 ng/ml) or TNF-α (50 ng/ml).

Experiments were performed to demonstrate the agonistic, synergistic effects of TWEAK and TNF-α. Human fibroblast-like synoviocytes were treated with varying concentrations of TWEAK alone, TNF-α alone, or a combination of TWEAK and TNF-α, and the level of RANTES production with each treatment was measured by ELISA. Both TWEAK and TNF-α induced RANTES production. However, when TWEAK and TNF-α were administered in combination, a synergistic level of RANTES production resulted. Thus, TWEAK and TNF-α can synergize to induce expression of particular inflammatory genes.

Example 8

Genes Induced by TWEAK and TNF-α Combination Treatment in Normal Synoviocytes

Synoviocytes from a healthy donor were cultured in vitro and treated with 5 ng/ml TWEAK and 0.5 ng/ml TNF-α. Table 3 lists genes whose expression was affected by the treatment with TWEAK and TNF-α to a statistically significant degree. The genes are grouped by their gene ontology category.

TABLE 3

| Go Ontology | Protein | P Value |
| --- | --- | --- |
| Positive regulation of IκB | CASP1, CFLAR, LGLAS9, Myd88, SECTM1, TNFSF10, TRIM38 | 5.81e−018 |
| Inflammatory Response | CCL3, CCL4, CCL7, CCL8, CXCL9, ILRN, Myd88, TLR3 | 9.94e−007 |
| Chemotaxis | CCL3, CCL4, CCL7, CCL8, CXCL9, ERG1, SOCS1 | 0.0003 |
| Interferon Response | IFI44, WARS, IRF2 | 0.001 |

The changes were identified as statistically significant Go categories based on hypergeometric mean.

Example 9

Genes Induced by TWEAK and TNF-α Combination Treatment in RA Synoviocytes

Synoviocytes from a rheumatoid arthritis patient donor were cultured in vitro and treated with 5 ng/ml TWEAK and 0.5 ng/ml TNF-α. Table 4 lists genes whose expression was affected by the treatment with TWEAK and TNF-α to a statistically significant degree. The genes are grouped by their gene ontology category.

TABLE 4

| Go Ontology | Protein | pValue |
| --- | --- | --- |
| Inflammatory Response | CXCL10, CXCL3, PTGS2, APOL3 | 4.26e−005 |
| Response to Stress | CXCL10, CXCL3, PTGS2, APOL3, MDA5, MX1, PTGES, Rig-1 | 5.56e−006 |
| Response to biotic stimuli | CXCL10, CXCL3, PTGS2, APOL3, MDA5, MX1, PTGES, Rig-1, GBp1 | 3.69e−009 |

The changes were identified as statistically significant Go categories based on hypergeometric mean.

Example 10

P2D10 is an exemplary murine anti-TWEAK antibody. The sequence of the murine P2D10 heavy chain variable domain (SEQ ID NO:3), with CDRs underlined is:

```
  1 EVQLVESGGG LVRPGGSLKL FCAASGFTFS RYAMSWVRQS
    PEKRLEWVAE

51 ISSGGSYPYY PDTVTGRFTI SRDNAKNTLY LEMSSLKSED
    TAMYYCARVL

101 YYDYDGDRIE VMDYWGQGTA VIVSS
```

This is a murine subgroup 3D heavy chain variable domain.
The sequence of the murine P2D10 light chain variable domain (SEQ ID NO:4), with CDRs underlined is:

```
  1 DVVMTQSPLS LSVSLGDQAS ISCRSSQSLV SSKGNTYLHW
    YLQKPGQSPK

51 FLIYKVSNRF SGVPDRFSGS GSGTDFTLKI SRVAAEDLGV
    YFCSQSTHFP

101 RTFGGGTTLE IK
```

This is a murine subgroup 2 kappa light chain.
This is an exemplary amino acid sequence of the mature huP2D10 H1 IgG1 heavy chain (SEQ ID NO:5):

```
  1 EVQLVESGGG LVQPGGSLRL SCAASGFTFS RYAMSWVRQA
    PGKGLEWVAE

51 ISSGGSYPYY PDTVTGRFTI SRDNAKNSLY LQMNSLRAED
    TAVYYCARVL

101 YYDYDGDRIE VMDYWGQGTL VTVSSASTKG PSVFPLAPSS
    KSTSGGTAAL

151 GCLVKDYFPE PVTVSWNSGA LTSGVHTFPA VLQSSGLYSL
    SSVVTVPSSS

201 LGTQTYICNV NHKPSNTKVD KKVEPKSCDK THTCPPCPAP
    ELLGGPSVFL

251 FPPKPKDTLM ISRTPEVTCV VVDVSHEDPE VKFNWYVDGV
    EVHNAKTKPR

301 EEQYNSTYRV VSVLTVLHQD WLNGKEYKCK VSNKALPAPI
    EKTISKAKGQ

351 PREPQVYTLP PSRDELTKNQ VSLTCLVKGF YPSDIAVEWE
    SNGQPENNYK
```

```
401 TTPPVLDSDG SFFLYSKLTV DKSRWQQGNV FSCSVMHEAL
    HNHYTQKSLS
451 LSPG
```

This is an exemplary amino acid sequence of the mature huP2D10 L1 light chain (SEQ ID NO:6):

```
  1 DVVMTQSPLS LPVTPGEPAS ISCRSSQSLV SSKGNTYLHW
    YLQKPGQSPQ
 51 FLIYKVSNRF SGVPDRFSGS GSGTDFTLKI SRVEAEDVGV
    YFCSQSTHFP
101 RTFGGGTKVE IKRTVAAPSV FIFPPSDEQL KSGTASVVCL
    LNNFYPREAK
151 VQWKVDNALQ SGNSQESVTE QDSKDSTYSL SSTLTLSKAD
    YEKHKVYACE
201 VTHQGLSSPV TKSFNRGEC
```

This is an exemplary amino acid sequence of the mature huP2D10 L2 light chain (SEQ ID NO:7):

```
  1 DVVMTQSPLS LPVTPGEPAS ISCRSSQSLV SSKGNTYLHW
    YLQKPGQSPQ
 51 LLIYKVSNRF SGVPDRFSGS GSGTDFTLKI SRVEAEDVGV
    YYCSQSTHFP
101 RTFGGGTKVE IKRTVAAPSV FIFPPSDEQL KSGTASVVCL
    LNNFYPREAK
151 VQWKVDNALQ SGNSQESVTE QDSKDSTYSL SSTLTLSKAD
    YEKHKVYACE
201 VTHQGLSSPV TKSFNRGEC
```

A number of embodiments of the invention have been described. Nevertheless, it will be understood that various modifications may be made without departing from the spirit and scope of the invention. Accordingly, other embodiments are within the scope of the following claims.

---

What is claimed is:

1. A method for treating inflammatory bowel disease comprising: administering to a human subject who has inflammatory bowel disease, a TWEAK (TNF-like weak inducer of apoptosis) blocking agent selected from the group consisting of a monoclonal, chimeric, human, or humanized antibody that binds to TWEAK, and a soluble form of a TWEAK receptor, in combination with a TNF-α blocking agent selected from the group consisting of a monoclonal, chimeric, human, or humanized antibody that binds to TNF-α, and a soluble form of a TNF-α receptor, in amounts and for a time to provide a therapeutic effect.

2. The method of claim 1, wherein the inflammatory bowel disease is ulcerative colitis.

3. The method of claim 1, wherein the inflammatory bowel disease is Crohn's disease.

4. The method of claim 1, wherein the TWEAK blocking agent and the TNF-α blocking agent are administered in an amount effective to inhibit TWEAK and TNF-α pathways in cells that generate inflammatory signals.

5. The method of claim 1, wherein the TWEAK blocking agent and the TNF-α blocking agent are administered in an amount effective to reduce transcription of genes induced by TWEAK and TNF-α in cells that generate inflammatory signals.

6. The method of claim 5, wherein the genes induced by TWEAK and TNF-α are synergistically activated by TWEAK and TNF-α.

7. The method of claim 1, wherein the TWEAK blocking agent is administered at a dosage that is equal to or less than an amount required for efficacy with the TWEAK blocking agent monotherapy.

8. The method of claim 7, wherein the TWEAK blocking agent is administered at a dosage that is at least 10% less than an amount required for efficacy with the TWEAK blocking agent monotherapy.

9. The method of claim 1, wherein the TNF-α blocking agent is administered at a dosage that is equal to or less than an amount required for efficacy with the TNF-α blocking agent monotherapy.

10. The method of claim 9, wherein the TNF-α blocking agent is administered at a dosage that is at least 10% less than an amount required for efficacy with TNF-α blocking agent monotherapy.

11. The method of claim 1, wherein the TWEAK blocking agent reduces the ability of TWEAK to bind to a TWEAK receptor.

12. The method of claim 1, wherein the TWEAK blocking agent is a monoclonal, chimeric, human, or humanized antibody that binds to TWEAK.

13. The method of claim 12, wherein the antibody that binds to TWEAK comprises a heavy chain variable domain comprising:
  a) a complementarity determining region (CDR) 1 set forth as the amino acid sequence of amino acids 26 to 35 of SEQ ID NO:3 (GFTFSRYAMS);
  b) a CDR 2 set forth as the amino acid sequence of amino acids 50 to 66 of SEQ ID NO:3 (EISSGGSYPYYP-DTVTG); and
  c) a CDR 3 set forth as the amino acid sequence of amino acids 99 to 114 of SEQ ID NO:3 (VLYY-DYDGDRIEVMDY);
and a light chain variable domain comprising:
  a) a CDR 1 set forth as the amino acid sequence of amino acids 24 to 39 of SEQ ID NO:4 (RSSQSLVSSKGN-TYLH);
  b) a CDR 2 set forth as the amino acid sequence of amino acids 55 to 61 of SEQ ID NO:4 (KVSNRFS); and
  c) a CDR 3 set forth as the amino acid sequence of amino acids 94 to 102 of SEQ ID NO:4 (SQSTHFPRT).

14. The method of claim 13, wherein the antibody comprises a first amino acid sequence set forth in SEQ ID NO:5 and a second amino acid sequence set forth in SEQ ID NO:6 or SEQ ID NO:7.

15. The method of claim 1, wherein the TWEAK blocking agent is a soluble form of a TWEAK receptor.

16. The method of claim 15, wherein the soluble form of the TWEAK receptor comprises an antibody Fc region.

17. The method of claim 1, wherein the TNF-α blocking agent reduces the ability of TNF-α to bind to a TNF-α receptor.

18. The method of claim 1, wherein the TNF-α blocking agent is a monoclonal, chimeric, human, or humanized antibody that binds to TNF-α.

19. The method of claim 18, wherein the TNF-α blocking agent is infliximab or adalimumab.

20. The method of claim 1, wherein the TNF-α blocking agent is a soluble form of a TNF-α receptor.

21. The method of claim 1, wherein the TNF-α blocking agent is etanercept.

22. The method of claim 1, wherein the TWEAK blocking agent and the TNF-α blocking agent are administered to the subject at the same time.

23. The method of claim 22, wherein the TWEAK blocking agent and the TNF-α blocking agent are administered as a co-formulation.

24. The method of claim 1, wherein the TWEAK blocking agent and the TNF-α blocking agent are administered sequentially.

25. The method of claim 24, wherein the TWEAK blocking agent is administered to a patient who has already received the TNF-α blocking agent, wherein the TNF-α blocking agent is present at a therapeutic level in the subject.

26. The method of claim 24, wherein the TNF-α blocking agent is administered to a patient who has already received the TWEAK blocking agent, wherein the TWEAK blocking agent is present at a therapeutic level in the subject.

* * * * *

SEQUENCE LISTING

```
<160> NUMBER OF SEQ ID NOS: 7

<210> SEQ ID NO 1
<211> LENGTH: 249
<212> TYPE: PRT
<213> ORGANISM: Homo sapiens

<400> SEQUENCE: 1

Met Ala Ala Arg Arg Ser Gln Arg Arg Gly Arg Arg Gly Glu Pro
  1               5                  10                  15

Gly Thr Ala Leu Leu Val Pro Leu Ala Leu Gly Leu Gly Leu Ala Leu
                 20                  25                  30

Ala Cys Leu Gly Leu Leu Leu Ala Val Val Ser Leu Gly Ser Arg Ala
                 35                  40                  45

Ser Leu Ser Ala Gln Glu Pro Ala Gln Glu Glu Leu Val Ala Glu Glu
 50                  55                  60

Asp Gln Asp Pro Ser Glu Leu Asn Pro Gln Thr Glu Glu Ser Gln Asp
 65                  70                  75                  80

Pro Ala Pro Phe Leu Asn Arg Leu Val Arg Pro Arg Arg Ser Ala Pro
                 85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
                115                 120                 125

Thr Val Ser Gly Trp Glu Glu Ala Arg Ile Asn Ser Ser Ser Pro Leu
                130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
                180                 185                 190

Glu Glu Phe Ser Ala Thr Ala Ala Ser Ser Leu Gly Pro Gln Leu Arg
                195                 200                 205

Leu Cys Gln Val Ser Gly Leu Leu Ala Leu Arg Pro Gly Ser Ser Leu
                210                 215                 220
```

```
Arg Ile Arg Thr Leu Pro Trp Ala His Leu Lys Ala Ala Pro Phe Leu
225                 230                 235                 240

Thr Tyr Phe Gly Leu Phe Gln Val His
                245
```

<210> SEQ ID NO 2
<211> LENGTH: 129
<212> TYPE: PRT
<213> ORGANISM: Homo sapiens

<400> SEQUENCE: 2

```
Met Ala Arg Gly Ser Leu Arg Arg Leu Leu Arg Leu Leu Val Leu Gly
 1               5                  10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln
```

<210> SEQ ID NO 3
<211> LENGTH: 125
<212> TYPE: PRT
<213> ORGANISM: Mus musculus

<400> SEQUENCE: 3

```
Glu Val Gln Leu Val Glu Ser Gly Gly Gly Leu Val Arg Pro Gly Gly
 1               5                  10                  15

Ser Leu Lys Leu Phe Cys Ala Ala Ser Gly Phe Thr Phe Ser Arg Tyr
                20                  25                  30

Ala Met Ser Trp Val Arg Gln Ser Pro Glu Lys Arg Leu Glu Trp Val
            35                  40                  45

Ala Glu Ile Ser Ser Gly Gly Ser Tyr Pro Tyr Pro Asp Thr Val
50                  55                  60

Thr Gly Arg Phe Thr Ile Ser Arg Asp Asn Ala Lys Asn Thr Leu Tyr
65                  70                  75                  80

Leu Glu Met Ser Ser Leu Lys Ser Glu Asp Thr Ala Met Tyr Tyr Cys
                85                  90                  95

Ala Arg Val Leu Tyr Tyr Asp Tyr Asp Gly Asp Arg Ile Glu Val Met
            100                 105                 110

Asp Tyr Trp Gly Gln Gly Thr Ala Val Ile Val Ser Ser
        115                 120                 125
```

<210> SEQ ID NO 4
<211> LENGTH: 112
<212> TYPE: PRT
<213> ORGANISM: Mus musculus

<400> SEQUENCE: 4

```
Asp Val Val Met Thr Gln Ser Pro Leu Ser Leu Ser Val Ser Leu Gly
1               5                   10                  15

Asp Gln Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Ala Ala Glu Asp Leu Gly Val Tyr Phe Cys Ser Gln Ser
                85                  90                  95

Thr His Phe Pro Arg Thr Phe Gly Gly Gly Thr Thr Leu Glu Ile Lys
            100                 105                 110
```

<210> SEQ ID NO 5
<211> LENGTH: 454
<212> TYPE: PRT
<213> ORGANISM: Artificial sequence
<220> FEATURE:
<223> OTHER INFORMATION: Synthetically generated peptide

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu Val Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145             150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225             230                 235                 240

Glu Leu Leu Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly
    450

<210> SEQ ID NO 6
<211> LENGTH: 219
<212> TYPE: PRT
<213> ORGANISM: Artificial sequence
<220> FEATURE:
<223> OTHER INFORMATION: Synthetically generated peptide

<400> SEQUENCE: 6

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                    165                 170                 175
Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 7
<211> LENGTH: 219
<212> TYPE: PRT
<213> ORGANISM: Artificial sequence
<220> FEATURE:
<223> OTHER INFORMATION: Synthetically generated peptide

<400> SEQUENCE: 7

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```